(12) United States Patent
Ignatyev et al.

(10) Patent No.: US 8,148,443 B2
(45) Date of Patent: Apr. 3, 2012

(54) OXONIUM AND SULFONIUM SALTS

(75) Inventors: Nikolai (Mykola) Ignatyev, Duisburg (DE); German Bissky, Wuppertal (DE); Helge Willner, Muelheim/Ruhr (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 0 days.

(21) Appl. No.: 12/908,479

(22) Filed: Oct. 20, 2010

(65) Prior Publication Data

US 2011/0034698 A1    Feb. 10, 2011

Related U.S. Application Data

(63) Continuation of application No. 12/278,213, filed as application No. PCT/EP2007/000051 on Jan. 5, 2007, now Pat. No. 7,842,804.

(30) Foreign Application Priority Data

Feb. 4, 2006 (DE) .......................... 10 2006 005 103

(51) Int. Cl.
*C07C 311/48* (2006.01)
*C07C 381/12* (2006.01)
*C07F 5/02* (2006.01)
*C07F 9/52* (2006.01)
*C07D 211/00* (2006.01)
*C07D 221/00* (2006.01)
*C07D 239/00* (2006.01)
*C07D 241/00* (2006.01)
*C07D 207/00* (2006.01)
*C07D 209/00* (2006.01)

(52) U.S. Cl. ................ 522/31; 522/25; 522/15; 522/63; 544/229; 544/242; 544/336; 546/184; 548/400; 548/560; 548/564; 568/1; 568/8; 568/16

(58) Field of Classification Search ............... 522/25, 522/31, 63, 64; 544/242, 336, 229; 546/184; 548/560, 564, 400; 568/1, 8, 16

See application file for complete search history.

(56) References Cited

U.S. PATENT DOCUMENTS

| | | | |
|---|---|---|---|
| 2,946,770 A | 7/1960 | Bader et al. | |
| 5,668,192 A * | 9/1997 | Castellanos et al. | 522/31 |
| 5,827,602 A | 10/1998 | Koch et al. | |
| 6,340,716 B1 * | 1/2002 | Armand et al. | 522/31 |
| 6,423,378 B1 | 7/2002 | Cotting et al. | |
| 6,863,838 B2 * | 3/2005 | Hamrock | 252/62.2 |
| 6,911,297 B2 | 6/2005 | Brzozowy et al. | |
| 6,951,831 B2 | 10/2005 | Lecocq et al. | |
| 7,153,974 B2 | 12/2006 | Schmidt et al. | |
| 7,192,991 B2 * | 3/2007 | Kropp et al. | 522/25 |
| 7,276,622 B2 * | 10/2007 | Hagiya | 560/124 |
| 7,480,778 B2 * | 1/2009 | Somavarapu | 711/159 |
| 7,501,522 B2 * | 3/2009 | Maase et al. | 548/102 |
| 7,605,297 B2 | 10/2009 | Maase et al. | |
| 7,687,513 B1 | 3/2010 | Muldoon et al. | |
| 7,709,598 B2 | 5/2010 | Kimura et al. | |
| 2003/0060359 A1 | 3/2003 | Olivier-Bourbigou et al. | |
| 2003/0148211 A1 | 8/2003 | Kamabuchi et al. | |
| 2003/0220191 A1 | 11/2003 | Lecocq et al. | |
| 2004/0045874 A1 | 3/2004 | Olivier-Bourbigou et al. | |
| 2005/0103706 A1 | 5/2005 | Bennett et al. | |
| 2006/0149074 A1 | 7/2006 | Maase et al. | |
| 2007/0085062 A1 | 4/2007 | Gordon | |
| 2007/0099079 A1 | 5/2007 | Matsumoto et al. | |
| 2007/0197677 A1 | 8/2007 | Tsuchimura et al. | |
| 2007/0225458 A1 | 9/2007 | Kimura et al. | |
| 2007/0255064 A1 | 11/2007 | Szarvas et al. | |
| 2007/0281209 A1 | 12/2007 | Kishi et al. | |
| 2008/0008930 A1 | 1/2008 | Matsumoto et al. | |
| 2008/0192801 A1 | 8/2008 | Gordon | |
| 2009/0163723 A1 | 6/2009 | Kimura et al. | |
| 2010/0023353 A1 * | 1/2010 | Stoffiere | 705/4 |

FOREIGN PATENT DOCUMENTS

| | | |
|---|---|---|
| EP | 1679307 A | 7/2006 |
| FR | 2727416 A1 | 5/1996 |
| GB | 2387127 A | 10/2003 |
| JP | 2004123631 A2 | 4/2004 |
| JP | 2005275153 A2 | 10/2005 |
| JP | 2006258925 A2 | 9/2006 |
| WO | WO 2004002955 A2 | 1/2004 |
| WO | WO 2005116038 A1 | 12/2005 |

OTHER PUBLICATIONS

Matsumoto et al,"Preparation of room temperature ionic liquids based on aliphatic onium cations and asymmetric amide anions and their electrochemical properties as a lithium battery electrolyte", Journal of power sources, Elsevier, Amsterdam, NL, Bd 146, Nr 1-2, Aug. 26, 2005, Seiten 45-50, XP005076585.
Lee et al,"Perflourosulfonyl imides and methides investigating the lithographic potential of novel superacid PAGs", Proceedings of the Spie, SPIE, Bellingham, VA, US, Bd 4690, Nr 1, Mar. 2002, Seiten 169-177, XP002309548.
Okoturo et al,"Temperature dependence of viscosity for room temperature ionic liquids", Journal of electroanalytical chemistry and interfacial electrochemistry, Elsevier, Amsterdam, NL, Bd 568, 2004, Seiten 167-181, XP002334479.
Matsumoto et al,"Room temperature molten salts based on trialkyisulfonium cations and bis(triflouromethylsulfonyl)imide", Chemistry letters, 12, 1430-1431, 2000, XP009088266.

* cited by examiner

*Primary Examiner* — Susan W Berman
(74) *Attorney, Agent, or Firm* — Millen, White, Zelano & Branigan, P.C.

(57) ABSTRACT

The present invention relates to oxonium salts having $[(R°)_3O]^+$ cations and sulfonium salts having $[(R°)_3S]^+$ cations, where R° denotes straight-chain or branched alkyl groups having 1-8 C atoms or phenyl which is unsubstituted or substituted by R°, OR°, $N(R°)_2$, CN or halogen, and anions selected from the group of $[PF_x(C_yF_{2y+1-x}H_z)_{6-x}]^-$ anions, where $2 \leq x \leq 5$, $1 \leq y \leq 8$ and $0 \leq z \leq 2y+1$, or anions selected from the group of $[BF_n(CN)_{4-n}]^-$ anions, where n=0, 1, 2 or 3, or anions selected from the group of $[(R^{f1}SO_2)_2N]^-$ anions or anions selected from the group of $[BF_nR^{f2}_{4-w}]^-$ anions, to processes for the preparation thereof, and to the use thereof, in particular for the preparation of ionic liquids.

24 Claims, No Drawings

OXONIUM AND SULFONIUM SALTS

This application is a continuation application of U.S. Ser. No. 12/278,213 filed Aug. 4, 2008, now U.S. Pat. No. 7,842, 804, which is a 371 filing of Application PCT/EP2007/ 000051 filed Jan. 5, 2007 which claims priority to German Application 102006005103.2, filed Feb. 4, 2007.

The present invention relates to oxonium salts having $[(R^{o})_3 O]^+$ cations and sulfonium salts having $[(R^{o})_3 S]^+$ cations, where $R^{o}$ denotes straight-chain or branched alkyl groups having 1-8 C atoms or phenyl which is unsubstituted or substituted by $R^{o}$, $OR^{o}$, $N(R^{o})_2$, CN or halogen, and anions selected from the group of $[PF_x(C_yF_{2y+1-z}H_z)_{6-x}]^-$ anions, where $2 \leq x \leq 5$, $1 \leq y \leq 8$ and $0 \leq z \leq 2y+1$, or anions selected from the group of $[BF_n(CN)_{4-n}]^-$ anions, where n=0, 1, 2 or 3, or anions selected from the group of $[(R^{f1}SO_2)_2N]^-$ anions or anions selected from the group of $[BF_w R^{f2}_{4-w}]^-$ anions, to processes for the preparation thereof, and to the use thereof, in particular for the preparation of ionic liquids.

Owing to their properties, ionic liquids represent an effective alternative to traditional volatile organic solvents for organic synthesis in modern research. The use of ionic liquids as novel reaction medium could furthermore be a practical solution both for solvent emission and also for problems in the reprocessing of catalysts.

Ionic liquids or liquid salts are ionic species which consist of an organic cation and a generally inorganic anion. They do not contain any neutral molecules and usually have melting points below 373 K. However, the melting point may also be higher without restricting the usability of the salts in all areas of application. Examples of organic cations are, inter alia, tetraalkylammonium, tetraalkylphosphonium, N-alkylpyridinium, 1,3-dialkyl-imidazolium or trialkylsulfonium. Amongst a multiplicity of suitable anions, mention may be made, for example, of $BF_4^-$, $PF_6^-$, $SbF_6^-$, $NO_3^-$, $CF_3SO_3^-$, $(CF_3SO_2)_2N^-$, arylSO$_3^-$, $CF_3CO_2^-$, $CH_3CO_2^-$ or $Al_2Cl_7^-$.

The properties of ionic liquids, for example the melting point, the thermal and electrochemical stability or viscosity, are determined by the choice of the cations and anions. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetailkatalyse" [ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227).

A large number of onium salts having perfluoroalkylfluorophosphate, bis(perfluoroalkylsulfonyl)imide, perfluoroalkylborate or tetracyanoborate anions are ionic liquids.

Corresponding onium salts having the above-mentioned anions are usually produced by anion exchange, for example from an onium halide in aqueous media. However, this process route proves to be less practicable if the onium halide is unstable to water. This applies, for example, to a series of oxonium or sulfonium cations.

There is therefore a demand for access to onium salts having perfluoroalkylfluorophosphate, bis(perfluoroalkylsulfonyl)imide, perfluoroalkylborate or tetracyanoborate anions which does not have the above-mentioned disadvantages. Accordingly, the object of the present invention is the provision of an alternative synthetic process.

The above-mentioned object is achieved by oxonium salts and sulfonium salts in accordance with the present invention, and by the use thereof for the preparation of onium salts having the said anions.

The present invention accordingly relates firstly to oxonium salts having) $[(R^{o})_3 O]^+$ cations and sulfonium salts having $[(R^{o})_3 S]^+$ cations, where $R^{o}$ denotes straight-chain or branched alkyl groups having 1-8 C atoms or phenyl which is unsubstituted or substituted by $R^{o}$, $OR^{o}$, $N(R^{o})_2$, CN or halogen, and anions selected from the group of $[PF_x(C_yF_{2y+1-z}H_z)_{6-x}]^-$ anions, where $2 \leq x \leq 5$, $1 \leq y \leq 8$ and $0 \leq z \leq 2y+1$, or anions selected from the group of $[BF_n(CN)_{4-n}]^-$ anions, where n=0, 1, 2 or 3, or anions selected from the group of $[(R^{f1}SO_2)_2N]^-$ anions, where $R^{f1}$ denotes F or perfluorinated and straight-chain or branched alkyl having 1-20 C atoms, preferably having 1-12 C atoms, perfluorinated and straight-chain or branched alkenyl having 2-20 C atoms and one or more double bonds, perfluorinated and straight-chain or branched alkynyl having 2-20 C atoms and one or more triple bonds, perfluorinated and saturated, partially or fully unsaturated cycloalkyl having 3-7 C atoms, in particular phenyl, which may be substituted by perfluoroalkyl groups, or anions selected from the group of $[BF_w R^{f2}_{4-w}]^-$ anions, where w=0, 1, 2 or 3, where $R^{f2}$ denotes perfluorinated and straight-chain or branched alkyl having 1-20 C atoms, preferably having 1-12 C atoms, perfluorinated and straight-chain or branched alkenyl having 2-20 C atoms and one or more double bonds, perfluorinated and straight-chain or branched alkynyl having 2-20 C atoms and one or more triple bonds, perfluorinated and saturated, partially or fully unsaturated cycloalkyl having 3-7 C atoms, in particular phenyl, which may be substituted by perfluoroalkyl groups, where $R^{f1}$ or $R^{f2}$ may in each case be identical or different,
where $R^{f1}$ or $R^{f2}$ may be connected to one another in pairs by single or double bonds,
and where, in $R^{f1}$ or $R^{f2}$, one or two non-adjacent carbon atoms which are not in the α-position to the heteroatom may be replaced by atoms and/or atom groups selected from the group —O—, —SO$_2$— and —NR'— or by the end group —SO$_2$X', where R'=non-, partially or perfluorinated $C_1$- to $C_6$-alkyl, $C_3$- to $C_7$-cycloalkyl, unsubstituted or substituted phenyl, including —$C_6F_5$, and X'=F, Cl or Br.

Suitable anions in the oxonium salts according to the invention are, for example, $[(CF_3SO_2)_2N]^-$, $[(C_2F_5SO_2)_2N]^-$, $[(FSO_2)_2N]^-$, $[P(C_2F_5)_3F_3]^-$, $[P(CF_3)_3F_3]^-$, $[P(C_2F_4H)(CF_3)_2F_3]^-$, $[P(C_2F_3H_2)_3F_3]^-$, $[P(C_2F_5)(CF_3)_2F_3]^-$, $[P(C_3F_7)_3F_3]^-$, $[P(C_4F_9)_3F_3]^-$, $[P(C_2F_5)_2F_4]^-$, $[BF_3(CF_3)]^-$, $[BF_2(C_2F_5)_2]^-$, $[BF_3(C_2F_5)]^-$, $[BF_2(CF_3)_2]^-$, $[B(C_2F_5)_4]^-$, $[BF_3(CN)]^-$, $[BF_2(CN)_2]^-$, $[B(CN)_4]^-$, $[B(CF_3)_4]^-$. Very preferred anions from this group are $[(CF_3SO_2)_2N]^-$, $[(C_2F_5SO_2)_2N]^-$, $[B(CN)_4]^-$, $[(C_2F_5)_3PF_3]^-$, $[(C_2F_5)_2PF_4]^-$, $[(C_4F_9)_3PF_3]^-$, $[(C_3F_7)_3PF_3]^-$, $[B(C_2F_5)F_3]^-$ or $[B(CF_3)_4]^-$. Very particularly preferred anions from this group are $[(CF_3SO_2)_2N]^-$, $[B(CN)_4]^-$, $[(C_2F_5)_3PF_3]^-$ or $[B(C_2F_5)F_3]^-$.

$R^{o}$ of the $[(R^{o})_3 O]^+$ cation or $[(R^{o})_3 S]^+$ cation is preferably straight-chain alkyl having 1-8 C atoms, preferably having 1-4 C atoms, in particular methyl or ethyl, very particularly preferably ethyl.

The present invention furthermore relates to a process for the preparation of the oxonium salts and sulfonium salts according to the invention having $[PF_x(C_yF_{2y+1-z}H_z)_{6-x}]^-$ anions or of onium salts comprising organic cations with $[PF_x(C_yF_{2y+1-z}H_z)_{6-x}]^-$ anions, where an $[(R^{o})_3 O]^+$ tetrafluoroborate or hexafluorophosphate or an $[(R^{o})_3 S]^+$ tetrafluoroborate or hexafluorophosphate or an onium tetrafluoroborate or hexafluorophosphate is reacted with a phosphorane of the general formula $PF_a(C_yF_{2y+1-z}H_z)_{5-a}$, where $1 \leq a \leq 4$, and $R^o$, y and z have the meaning indicated above.

The phosphoranes employed in the process according to the invention are accessible, for example, via electrochemical fluorination of alkylphosphoranes or alkylphosphines. Processes of this type are known to the person skilled in the art, for example from EP 1 037 896. Besides the oxonium and sulfonium salts according to the invention, the process according to the invention also gives access to other onium salts having $[PF_x(C_yF_{2y+1-z}H_z)_{6-x}]^-$ anions. The previous synthesis of these onium salts is carried out, for example, by reaction of corresponding onium halides with corresponding lithium perfluoroalkylfluorophosphates. These processes have the disadvantage that the principal product is contaminated with lithium halide. The process according to the invention gives simpler access to corresponding onium salts, which can be obtained with higher purity.

In onium salts having organic cations employed in the process according to the invention, the organic cation can be an ammonium, phosphonium, guanidinium, uranium, thiouronium cation or a heterocyclic cation. Suitable cations are mentioned and described later in this application in the description of analogous onium halides.

In an alternative variant, the oxonium salts and sulfonium salts according to the invention can be obtained by reaction of an $[(R^o)_3O]^+$ tetrafluoroborate or hexafluorophosphate or an $[(R^o)_3S]^+$ tetrafluoroborate or hexafluorophosphate with $H^+[PF_x(C_yF_{2y+1-z}H_z)_{6-x}]^-$, $H^+[BF_n(CN)_{4-n}]^-$, $H^+[(R^{f1}SO_2)_2N]^-$ or $H^+[BF_wR^{f2}_{4-w}]^-$ or with an alkali metal salt or alkaline-earth metal salt of $H^+[PF_x(C_yF_{2y+1-z}H_z)_{6-x}]^-$, $H^+[BF_n(CN)_{4-n}]^-$, $H^+[(R^{f1}SO_2)_2N]^+$ or $H^+[BF_wR^{f2}_{4-w}]^-$, where $R^o$, x, y, z, n, $R^{f1}$, $R^{f2}$ and w have the meaning indicated above.

Acids of the type $H^+[PF_x(C_yF_{2y+1-z}H_z)_{6-x}]^-$ can be prepared by synthetic methods as known from the literature, for example from EP 1 399 453. Corresponding acids of the type $H^+[BF_n(CN)_{4-n}]^-$ or $H^+[BF_wR^{f2}_{4-w}]^-$ can be obtained by the process described in German Application DE 10 2004 051 278.7.

Compounds of the type $H^+[(R^{f1}SO_2)_2N]^-$ are known, for example, from D. D. Desmarteau, M. Witz, J. Fluorine Chem, 52 (1991) p. 7-12; T. Netscher, W. Bonrath, A. Haas, E. Hoppmann, H. Pauling, Chimia, 58 (2004), p. 153-155.

The oxonium tetrafluoroborate having the formula $[(R^o)_3O]^+[BF_4]^-$ employed is preferably an oxonium tetrafluoroborate containing straight-chain or branched alkyl groups having 1-8 C atoms, preferably having 1-4 C atoms, which are in each case independent of one another. Preference is given to the use of oxonium tetrafluoroborates in which the alkyl groups are identical.

The sulfonium tetrafluoroborate having the formula $[(R^o)_3S]^+[BF_4]^-$ employed is preferably a sulfonium tetrafluoroborate containing straight-chain or branched alkyl groups having 1-8 C atoms, preferably having 1-4 C atoms, which are in each case independent of one another. Preference is given to the use of sulfonium tetrafluoroborates in which the alkyl groups are identical.

The oxonium tetrafluoroborates or sulfonium tetrafluoroborates employed are generally commercially available or can be prepared by synthetic methods as known from the literature, for example in the standard works, such as Houben-Weyl, Methoden der organischen Chemie [Methods of Organic Chemistry], Georg-Thieme-Verlag, Stuttgart, or Richard C. Larock, Comprehensive Organic Transformations, 2nd Edition, Wiley-VCH, New York, 1999. Use can also be made here of variants known per se which are not mentioned here in greater detail.

Examples of oxonium tetrafluoroborates are trimethyloxonium tetrafluoroborate, triethyloxonium tetrafluoroborate (Meerwein salt), tris(n-propyl)oxonium tetrafluoroborate, dimethylethyloxonium tetrafluoroborate, diethylmethyloxonium tetrafluoroborate or tris(i-propyl)oxonium tetrafluoroborate. Very particular preference is given to the use of trimethyl- or triethyloxonium tetrafluoroborate.

Examples of sulfonium tetrafluoroborates are trimethylsulfonium, triethylsulfonium, dimethylethylsulfonium, diethylmethylsulfonium, dipropylmethylsulfonium, dipropylethylsulfonium, dibutylmethylsulfonium, di-sec-butylmethylsulfonium, dibutylethylsulfonium tetrafluoroborate. Very particular preference is given to the use of trimethylsulfonium and triethylsulfonium tetrafluoroborate.

The processes according to the invention can be carried out in a solvent or without addition of a solvent. A suitable solvent is, for example, dichloromethane or diethyl ether.

The processes are preferably carried out without addition of a solvent,

The reaction temperatures are in the range from 0° C. to 150° C., preferably in the range from 50 to 100° C.

The oxonium salts and sulfonium salts according to the invention can be employed in a variety of ways and facilitate access to a multiplicity of derivatives. The present invention furthermore relates, in particular, to the use of the oxonium salts and sulfonium salts according to the invention for the preparation of onium salts comprising organic cations with $[PF_x(C_yF_{2y+1-z}H_z)_{6-x}]^-$, $[BF_n(CN)_{4-n}]^-$, $[(R^{f1}SO_2)_2N]^-$ or $[BF_wR^{f2}_{4-w}]^-$ anions, where x, y, z, n, $R^{f1}$, $R^{f2}$ and w have the meaning indicated above. Many of the onium salts prepared using the oxonium salts and sulfonium salts according to the invention are ionic liquids and thus of great interest for many applications. Overall, the provision of the oxonium salts and sulfonium salts according to the invention provides alternative access to common ionic liquids, or makes the synthesis of individual ionic liquids possible at all. This relates, in particular, to ionic liquids in which the cation is not stable in the aqueous media used in the usual synthetic methods.

The organic cation of the onium salts can be a tritylium, ammonium, phosphonium, guanidinium, uronium, thiouronium cation or a heterocyclic cation.

In the simplest case, the corresponding onium salts having $[PF_x(C_yF_{2y+1-z}H_z)_{6-x}]^-$, $[BF_w(CN)_{4-w}]^-$, $[(R^{f1}SO_2)_2N]^-$ or $[BF_wR^{f2}_{4-w}]^-$ anions are prepared by reaction of a corresponding onium halide of the organic cation with a corresponding oxonium salt or sulfonium salt in accordance with the present invention. In addition, the corresponding onium tetrafluoroborates or hexafluorophosphates are also suitable for the reaction with an oxonium or sulfonium salt according to the invention.

Ammonium or phosphonium halides can be described, for example, by the formula (1)

$$[XR_4]^+Hal^- \quad (1),$$

where
X denotes N, P
Hal denotes Cl, Br or I and
R in each case, independently of one another, denotes
H, where all substituents R cannot simultaneously be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms, where one or more R may be partially or fully substituted by F, but where all four or three R cannot be fully substituted by F, and where, in the R, one or two non-adjacent carbon atoms which are not in the α-position may be replaced by atoms and/or atom groups selected from the group —O—, —S—, —S(O)—, —SO$_2$— and —NR'— or by the end group CN, —C(O)X' or —SO$_2$X', where R'=H, non-, partially or perfluorinated C$_1$- to C$_6$-alkyl, C$_3$- to C$_7$-cycloalkyl, unsubstituted or substituted phenyl, or an unsubstituted or substituted heterocycle, and X'=OH, F, Cl or Br.

However, compounds of the formulae (1) in which all four or three substituents R are fully substituted by halogens, for example tris(trifluoromethyl)methylammonium chloride, tetra(trifluoromethyl)ammonium chloride or tetra(nonafluorobutyl)ammonium chloride, tris(trifluoromethyl)methylphosphonium chloride, tetra(trifluoromethyl)phosphonium chloride or tetra(nonafluorobutyl)phosphonium chloride, are excluded.

The corresponding ammonium or phosphonium tetrafluoroborates or hexafluorophosphates can likewise be employed in an analogous manner.

Uronium or thiouronium halides can be described, for example, by the formula (2)

$$[(R^1R^2N)—C(=XR^7)(NR^3R^4)]^+Hal^- \quad (2)$$

and guanidinium halides can be described, for example, by the formula (3)

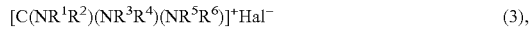

$$[C(NR^1R^2)(NR^3R^4)(NR^5R^6)]^+Hal^- \quad (3),$$

where

X in formula (2) denotes O or S,

Hal in formula (2) denotes Br or I and in formula (3) denotes Cl, Br or I, and

R$^1$ to R$^7$ each, independently of one another, denotes hydrogen or CN, where hydrogen is excluded for R$^7$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents R$^1$ to R$^7$ may be partially or fully substituted by F, but where all substituents on an N atom cannot be fully substituted by F, where the substituents R$^1$ to R$^7$ may be connected to one another in pairs by a single or double bond and where, in the substituents R$^1$ to R$^6$, one or two non-adjacent carbon atoms which are not bonded directly to the heteroatom may be replaced by atoms and/or atom groups selected from the group —O—, —S—, —S(O)—, —SO$_2$— and —NR'— or by the end group CN, —C(O)X' or —SO$_2$X', where R'=H, non-, partially or perfluorinated C$_1$- to C$_6$-alkyl, C$_3$- to C$_7$-cycloalkyl, unsubstituted or substituted phenyl, or an unsubstituted or substituted heterocycle, and X'=OH, F, Cl or Br.

Halides with a heterocyclic cation can be described, for example, by the formula (4)

$$[HetN]^+Hal^- \quad (4),$$

where

Hal denotes Cl, Br or I and

HetN$^+$ denotes a heterocyclic cation selected from the group

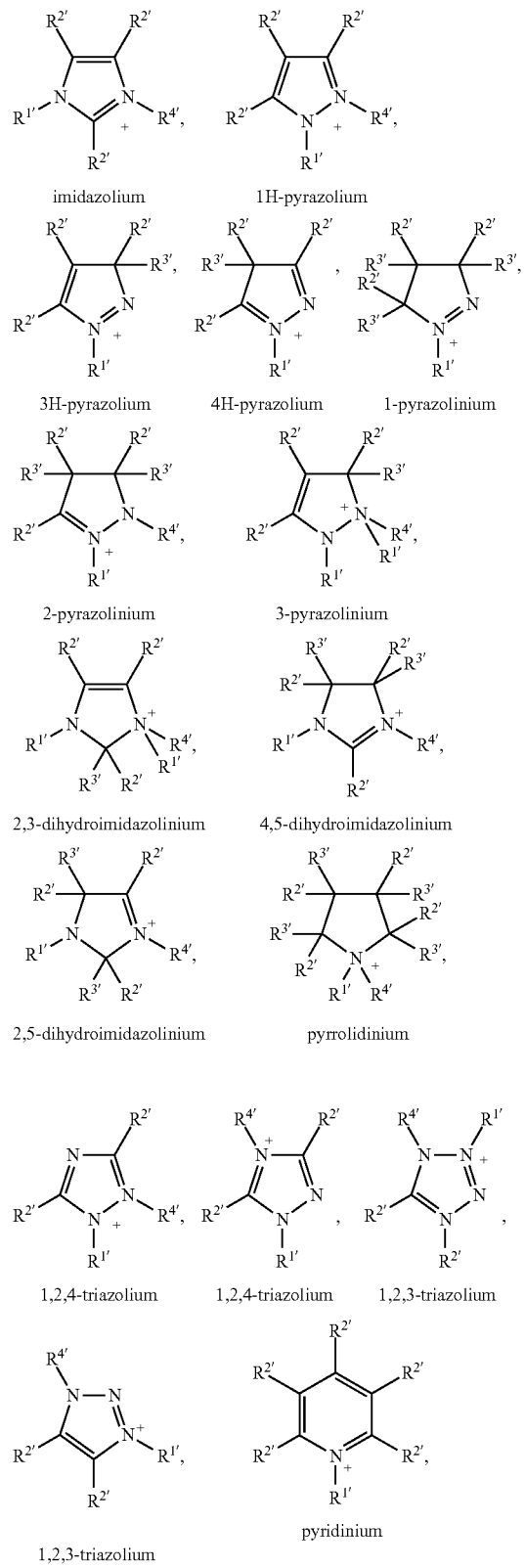

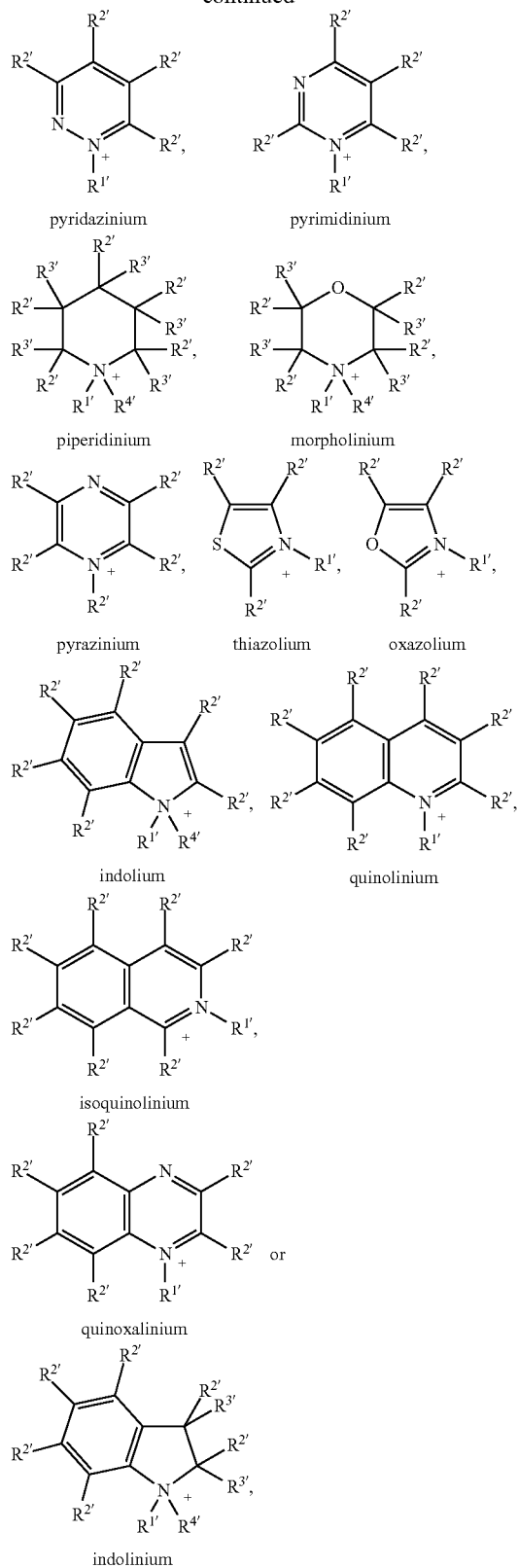

where the substituents

R$^{1'}$ to R$^{4'}$ each, independently of one another, denotes hydrogen or CN, straight-chain or branched alkyl having 1-20 C atoms, straight-chain or branched alkenyl having 2-20 C atoms and one or more double bonds, straight-chain or branched alkynyl having 2-20 C atoms and one or more triple bonds, dialkylamino containing alkyl groups having 1-4 C atoms, but which is not bonded to the heteroatom of the heterocycle.

saturated, partially or fully unsaturated cycloalkyl having 3-7 C atoms, which may be substituted by alkyl groups having 1-6 C atoms, or aryl-C$_1$-C$_6$-alkyl, where the substituents R$^{1'}$ and R$^{4'}$ may be partially or fully substituted by F, but where R$^{1'}$ and R$^{4'}$ cannot simultaneously be fully substituted by F, where the substituents R$^{1'}$ to R$^{4'}$ may be partially or fully substituted by OR', N(R')$_2$, CN or halogen and where, in R$^{1'}$ to R$^{4'}$, one or two non-adjacent carbon atoms which are not in the α-position to the heteroatom may be replaced by atoms and/or atom groups selected from the group —O—, —S—, —SO$_2$— and —NR'— or by the end group CN, —C(O)X' or —SO$_2$X', where R'=H, non-, partially or perfluorinated C$_1$- to C$_6$-alkyl, C$_3$- to C$_7$-cycloalkyl, unsubstituted or substituted phenyl, or an unsubstituted or substituted heterocycle, and X'=OH, F, Cl or Br.

For the purposes of the present invention, fully unsaturated substituents are also taken to mean aromatic substituents.

In accordance with the invention, suitable substituents R and R$^1$ to R$^7$ of the compounds of the formulae (1) to (3), besides hydrogen, are preferably: C$_1$- to C$_{20}$-, in particular C$_1$- to C$_{14}$-alkyl groups, and saturated or unsaturated, i.e. also aromatic, C$_3$- to C$_7$-cycloalkyl groups, which may be substituted by C$_1$- to C$_6$-alkyl groups, in particular phenyl. However, the substituents R and R$^1$ to R$^7$ may likewise be substituted by further functional groups, for example by CN, SO$_2$R', SO$_2$OR' or COOR'. R' denotes non-, partially or perfluorinated C$_1$- to C$_6$ alkyl, C$_3$- to C$_7$-cycloalkyl, unsubstituted or substituted phenyl.

The substituents R in the compounds of the formula (1) may be identical or different here. Preferably, three substituents in formula (1) are identical and one substituent is different.

The substituent R is particularly preferably methyl, ethyl, isopropyl, propyl, butyl, sec-butyl, pentyl, hexyl, octyl, decyl, tetradecyl or alkoxyalkyl, in which alkoxy denotes an —O—(C$_1$-C$_8$-alkyl).

Up to four substituents of the guanidinium cation may also be connected in pairs in such a way that mono-, bi- or polycyclic cations are formed.

Without restricting generality, examples of such guanidinium cations are:

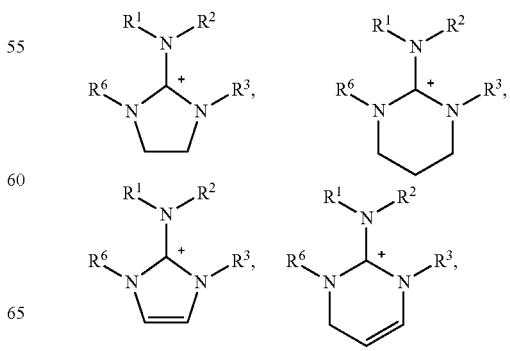

-continued

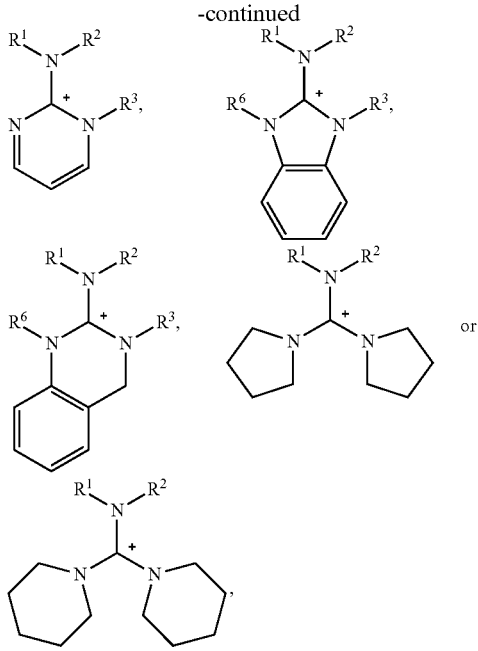

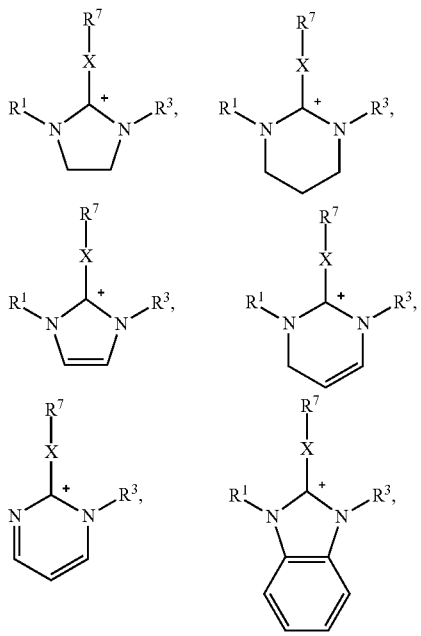

where the substituents $R^1$ to $R^3$ and $R^6$ can have an above-mentioned or particularly preferred meaning.

The carbocycles or heterocycles of the above-mentioned guanidinium cations may optionally also be substituted by $C_1$- to $C_6$-alkyl, $C_1$- to $C_6$-alkenyl, $NO_2$, F, Cl, Br, I, $C_1$-$C_6$-alkoxy, $SCF_3$, $SO_2CH_3$, $SO_2CF_3$, COOR", $SO_2NR"_2$, $SO_2X'$, $SO_3R"$, substituted or unsubstituted phenyl, where $X'$ and $R"$ have a meaning indicated above or below.

Up to four substituents of the of the uronium or thiouronium cation $[(R^1R^2N)-C(=XR^7)(NR^3R^4)]^+$ may also be connected in pairs in such a way that mono-, bi- or polycyclic cations are formed.

Without restricting generality, examples of such cations are indicated below:

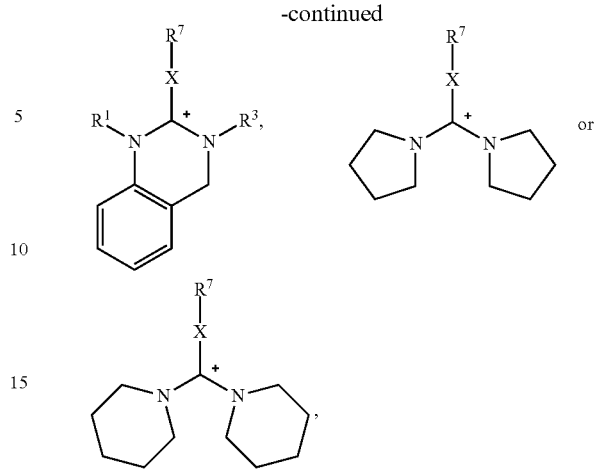

where X=O or S and the substituents, $R^1$, $R^3$ and $R^7$ can have an above-mentioned or particularly preferred meaning. The carbocycles or heterocycles of the above-mentioned guanidinium cations may optionally also be substituted by $C_1$- to $C_6$-alkyl, $C_1$- to $C_6$-alkenyl, $NO_2$, F, Cl, Br, I, $C_1$-$C_6$-alkoxy, $SCF_3$, $SO_2CH_3$, $SO_2CF_3$, COOR", $SO_2NR"_2$, $SO_2X'$, $SO_3R"$, substituted or unsubstituted phenyl, where $X'$ and $R"$ have a meaning indicated above or below.

The $C_1$-$C_{14}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl, dodecyl, tridecyl or tetradecyl. Optionally perfluorinated, for example as difluoromethyl, trifluoromethyl, pentafluoroethyl, heptafluoropropyl or nonafluorobutyl.

A straight-chain or branched alkenyl having 2 to 20 C atoms, where a plurality of double bonds may also be present, is, for example, vinyl, allyl, 2- or 3-butenyl, isobutenyl, sec-butenyl, furthermore 4-pentenyl, isopentenyl, hexenyl, heptenyl, octenyl, $-C_9H_{17}$, $-C_{10}H_{19}$ to $-C_{20}H_{39}$; preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, $-C_9H_{15}$, $-C_{10}H_{17}$ to $-C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted as described above by F, particularly preferably benzyl or phenylpropyl.

However, the phenyl ring or also the alkylene chain may likewise be substituted by further functional groups, for example by CN, $SO_2R'$, $SO_2OR'$ or COOR'. R' here has a meaning defined above.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the $C_1$- to $C_6$-alkyl-substituted cycloalkyl group may in turn also be substituted by halogen atoms, such as F, Cl, Br or I, in particular F or Cl, or $NO_2$. However, the cycloalkyl groups may likewise be substituted by further functional groups, for example by CN, $SO_2R'$, $SO_2OR'$ or COOR'. R' here has a meaning defined above.

In the substituents R, $R^1$ to $R^6$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —$SO_2$— and —NR'—, Without restricting generality, examples of substituents R, $R^1$ to $R^6$ and $R^{1'}$ to $R^{4'}$ modified in this way are: —$OCH_3$, —$OCH(CH_3)_2$, —$CH_2OCH_3$, —$CH_2$—$CH_2$—O—$CH_3$, —$C_2H_4OCH(CH_3)_2$, —$C_2H_4C_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —O—$C_4H_8$—O—$C_4H_9$, —$CF_3$, —$C_2F_5$, —$C_3F_7$, —$C_4F_9$, —$CF_2CF_2H$, —$CF_2CHFCF_3$, —$CF_2CH(CF_3)_2$, —$C_2F_4N(C_2F_5)C_2F_5$, —$CHF_2$, —$CH_2CF_3$, —$C_2F_2H_3$, —$C_3H_6$, —$CH_2C_3F_7$, —$CH_2C(O)OCH_3$, —$CH_2C_6H_5$ or —C(O)$C_6H_5$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, $C_1$-$C_6$-alkoxy, $SCF_3$, $SO_2CH_3$, $SO_2CF_3$, COOR'', $SO_2X'$, $SO_2NR''_2$ or $SO_3R''$, where X' denotes F, Cl or Br and R'' denotes a non- or partially fluorinated $C_1$- to $C_6$-alkyl or $C_3$- to $C_7$-cycloalkyl as defined for R', for example, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-methoxyphenyl, o-, m- or p-ethoxyphenyl, o-, m-, p-(trifluoromethyl)phenyl, o-, m-, p-(trifluoromethoxy)phenyl, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

The substituents $R^1$ to $R^7$ are each, independently of one another, preferably a straight-chain or branched alkyl group having 1 to 10 C atoms. The substituents $R^1$ and $R^2$, $R^3$ and $R^4$ and $R^5$ and $R^6$ in compounds of the formulae (2) and (3) may be identical or different here.

$R^1$ to $R^7$ are particularly preferably each, independently of one another, methyl, ethyl, n-propyl, isopropyl, n-butyl, sec-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (4), besides hydrogen, are preferably: CN, $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl or aryl-$C_1$-$C_6$-alkyl or diaminoalkyl having $C_1$-$C_4$-alkyl groups, so long as this is not bonded to the heteroatom. However, the substituents $R^{1'}$ to $R^{4'}$, in particular $R^{2'}$ and $R^{3'}$, may likewise be substituted by further functional groups, for example by CN, $SO_2R'$, $SO_2OR'$ or COOR'. R' denotes H, non-, partially or perfluorinated $C_1$- to $C_6$-alkyl, $C_3$- to $C_7$-cycloalkyl, unsubstituted or substituted phenyl, or an unsubstituted or substituted heterocycle.

The substituents $R^{1'}$ and $R^{4'}$ are each, independently of one another, particularly preferably CN, alkoxyethyl, in which alkoxy denotes —O—($C_1$-$C_8$-alkyl), in particular methoxyethyl, methyl, ethyl, isopropyl, propyl, butyl, sec-butyl, pentyl, hexyl, octyl, decyl, cyclohexyl, phenyl, phenylpropyl or benzyl. They are very particularly preferably CN, methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular, hydrogen, methyl, ethyl, isopropyl, propyl, butyl, sec-butyl, tert-butyl, cyclohexyl, dimethylamino, diethylamino, methylethylamino, phenyl or benzyl. $R^{2'}$ is particularly preferably dimethylamino, hydrogen, methyl, ethyl, isopropyl, propyl, butyl, sec-butyl or tert-butyl. $R^{2'}$ and $R^{3'}$ are very particularly preferably hydrogen, dimethylamino or methyl.

HetN⁺ of the formula (4) is preferably

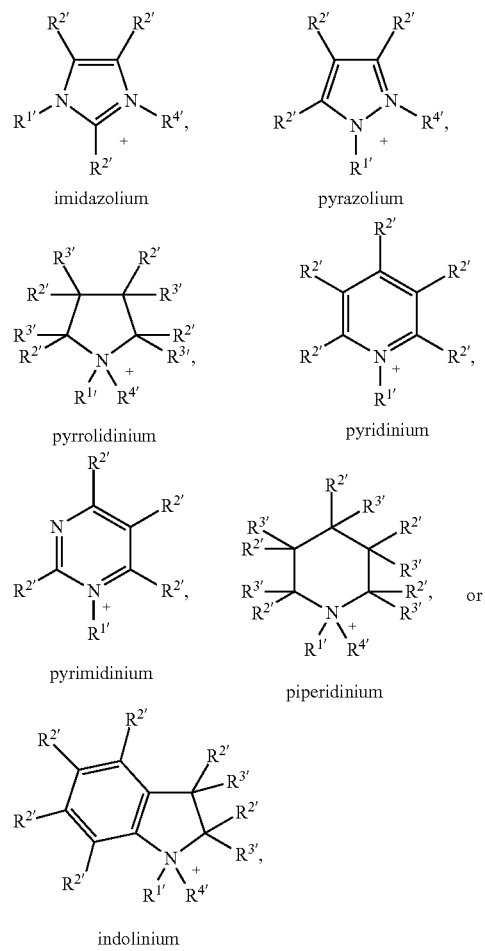

imidazolium pyrazolium pyrrolidinium pyridinium pyrimidinium piperidinium or indolinium where the substituents $R^{1'}$ to $R^{4'}$ each, independently of one another, have a meaning described above.

HetN⁺ is particularly preferably imidazolium, pyrrolidinium or pyridinium, as defined above, where the substituents $R^{1'}$ to $R^{4'}$ each, independently of one another, have a meaning described above.

The reaction between the oxonium salts and the onium halides, onium tetrafluoroborates, or hexafluorophosphates is usually carried out at temperatures between 0° C. and 100° C., preferably at 20° C. to 60° C., particularly preferably at room temperature. In the reaction with the sulfonium salts according to the invention, the reaction is carried out at temperatures between 0° C. and 150° C., preferably at 20° C. to 100° C. No solvent is required. However, it is also possible to employ solvents, for example dimethoxyethane, acetonitrile, dichloromethane, tetrahydrofuran, dimethyl sulfoxide, dioxane, propionitrile or mixtures with one another.

The reaction is carried out with an excess or equimolar amount of the corresponding oxonium salt or sulfonium salt according to the invention.

The reaction can be carried out at pressures between atmospheric pressure and 0.1 mbar. In order to accelerate the reaction, reduced pressures of down to 0.1 mbar are preferably employed. This applies, in particular, to reactions of onium bromides or iodides.

Besides the use for the preparation of ionic liquids, the oxonium salts and sulfonium salts according to the invention are also suitable as alkylating agents or as catalysts for cationic polymerisations or photochemically induced polymerisations, where sulfonium salts having triphenylsulfonium cations appear particularly suitable.

The present invention likewise relates to selected salts which, as described above, can be obtained by reaction with the oxonium and sulfonium salts according to the invention.

Accordingly, the present invention furthermore relates to the provision of salts (I) having cations selected from the group comprising

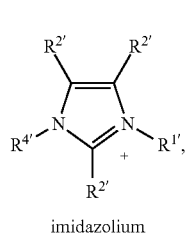
imidazolium

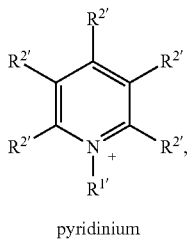
pyridinium

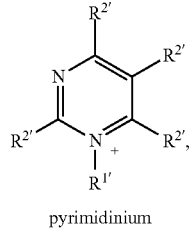
pyrimidinium

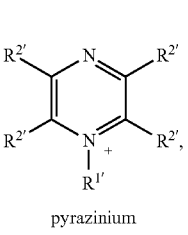
pyrazinium

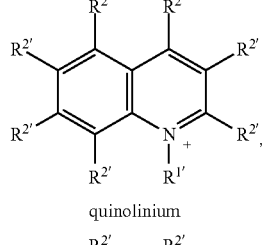
quinolinium

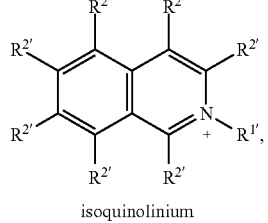
isoquinolinium or

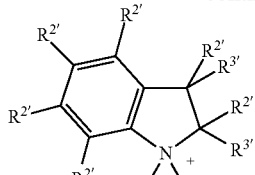
indolinium where the substituent
$R^{1'}$ denotes CN and $R^{2'}$ to $R^{4'}$ each, independently of one another, have the meaning
hydrogen,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
dialkylamino containing alkyl groups having 1-4 C atoms, which, however, is not bonded to the heteroatom of the heterocycle,
saturated, partially or fully unsaturated cycloalkyl having 3-7 C atoms,
which may be substituted by alkyl groups having 1-6 C atoms or aryl-$C_1$-$C_6$-alkyl,
where the substituents $R^{2'}$ and $R^{4'}$ may be partially or fully substituted by F,
where the substituents $R^{2'}$ and $R^{3'}$ may be partially or fully substituted by halogens or partially by $NO_2$ or CN,
and where, in the substituents $R^{2'}$ to $R^{4'}$, one or two non-adjacent carbon atoms which are not bonded directly to the heteroatom may be replaced by atoms and/or atom groups selected from the group —O—, —S—, —S(O)— or —$SO_2$—,
and anions selected from the group of $[PF_x(C_yF_{2y+1-z}H_z)_{6-x}]^-$ anions, where $2 \leq x \leq 5$, $1 \leq y \leq 8$ and $0 \leq z \leq 2y+1$,
or anions selected from the group of $[BF_n(CN)_{4-n}]^-$ anions, where n=0, 1, 2 or 3,
or anions selected from the group of $[(R^{f1}SO_2)_2N]^-$ anions, where $R^{f1}$ denotes F or perfluorinated and straight-chain or branched alkyl having 1-20 C atoms, perfluorinated and straight-chain or branched alkenyl having 2-20 C atoms and one or more double bonds, perfluorinated and straight-chain or branched alkynyl having 2-20 C atoms and one or more triple bonds, perfluorinated and saturated, partially or fully unsaturated cycloalkyl having 3-7 C atoms, which may be substituted by perfluoroalkyl groups, or anions selected from the group of $[BF_wR^{f2}_{4-w}]^-$ anions, where w=0, 1, 2 or 3, where $R^{f2}$ denotes perfluorinated and straight-chain or branched alkyl having 1-20 C atoms, perfluorinated and straight-chain or branched alkenyl having 2-20 C atoms and one or more double bonds, perfluorinated and straight-chain or branched alkynyl having 2-20 C atoms and one or more triple bonds, perfluorinated and saturated, partially or fully unsaturated cycloalkyl having 3-7 C atoms, which may be substituted by perfluoroalkyl groups,
where $R^{f1}$ or $R^{f2}$ may in each case be identical or different,
where $R^{f1}$ or $R^{f2}$ may be connected to one another in pairs by single or double bonds,
and where, in $R^{f1}$ or $R^{f2}$, one or two non-adjacent carbon atoms which are not in the α-position to the heteroatom may be replaced by atoms and/or atom groups selected from the group —O—, —$SO_2$— and —NR'— or by the end group —$SO_2X'$, where R'=non-, partially or perfluorinated $C_1$- to $C_6$-alkyl, $C_3$- to $C_7$-cycloalkyl, unsubstituted or substituted phenyl, or an unsubstituted or substituted heterocycle, and X'=F, Cl or Br.

The anion of the salts (I) is preferably selected from the group comprising $[(CF_3SO_2)_2N]^-$, $[(C_2F_5SO_2)_2N]^-$, $[(FSO_2)_2 N]^-$, $[P(C_2F_5)_3F_3]^-$, $[P(C_2F_4H)(CF_3)_2F_3]^-$, $[P(C_2F_3H_2)_3F_3]^-$, $[P(C_2F_5)(CF_3)_2F_3]^-$, $[P(C_3F_7)_3F_3]^-$, $[P(C_4F_9)_3F_3]^-$, $[P(C_2F_5)_2F_4]^-$, $[BF_3(CF_3)]^-$, $[BF_2(C_2F_5)_2]^-$, $[BF_3(C_2F_5)]^-$, $[BF_2(CF_3)]^-$, $[B(C_2F_5)_4]^-$, $[BF_3(CN)]^-$, $[BF_2(CN)_2]^-$, $[B(CN)_4]^-$, $[B(CF_3)_4]^-$ anions.

The said salts (I) are N-cyanopyridinium salts, N-cyanoimidazolium salts, N-cyanopyrazinium salts, N-cyanopyrimidinium salts, N-cyanoquinolinium salts, N-cyanoisoquinolinium salts, N-cyanoindolium salts, which can be employed in a variety of ways.

In the said salts (I), $R^{2'}$ to $R^{4'}$ is preferably selected from hydrogen, which is not bonded to the nitrogen, straight-chain or branched alkyl having 1-20 C atoms or from dialkylamino groups in which alkyl denotes $C_1$-$C_4$-alkyl.

The salts (I) are very particularly preferably the compounds 1-cyano-4-dimethylaminopyridinium tris(pentafluoroethyl)trifluorophosphate, 1-cyano-4-dimethylaminopyridinium bis(trifluoromethylsulfonyl)imide, 1-cyano-4-dimethylaminopyridinium tetracyanoborate and 1-cyano-4-dimethylaminopyridinium (pentafluoroothyl)trifluoroborate.

Furthermore, the invention likewise relates to salts (II) having cations selected from the group comprising

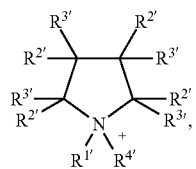

pyrrolidinium

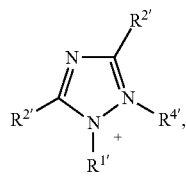

1, 2, 4-triazolium

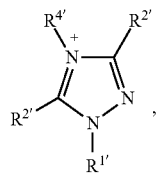

1, 2, 4-triazolium

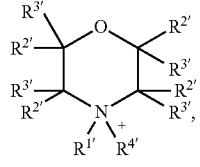

morpholinium piperidinium where the substituents
$R^{1'}$ to $R^{4'}$ each, independently of one another, have the meaning hydrogen or CN,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
dialkylamino containing alkyl groups having 1-4 C atoms, which, however, is not bonded to the heteroatom of the heterocycle,
saturated, partially or fully unsaturated cycloalkyl having 3-7 C atoms,
which may be substituted by alkyl groups having 1-6 C atoms or aryl-$C_1$-$C_6$-alkyl,
where the substituents $R^{1'}$ and $R^{4'}$ may be partially or fully substituted by F, but where $R^{1'}$ and $R^{4'}$ are not simultaneously CN or cannot simultaneously be fully substituted by F,
where the substituents $R^{2'}$ and $R^{3'}$ may be partially or fully substituted by halogens or partially by $NO_2$ or CN,
and where, in the substituents $R^{1'}$ to $R^{4'}$, one or two non-adjacent carbon atoms which are not bonded directly to the heteroatom may be replaced by atoms and/or atom groups selected from the group —O—, —S—, —S(O)—, —$SO_2$— and —NR'— or by the end group CN, —C(O)X' or —$SO_2$X', where R'=H, non-, partially or perfluorinated $C_1$- to $C_6$-alkyl, $C_3$- to $C_7$-cycloalkyl, unsubstituted or substituted phenyl, or an unsubstituted or substituted heterocycle, and X'=OH, F, Cl or Br, and anions selected from the group of $[PF_x(C_yF_{2y+1-z}H_z)_{6-x}]^-$ anions, where $2 \leq x \leq 5$, $1 \leq y \leq 8$ and $0 \leq z \leq 2y+1$, where 1-butyl-1-methylpyrrolidinium tris(pentafluoroethyl)trifluorophosphate is excluded.

The anion of the salts (II) is preferably selected from the group comprising $[P(C_2F_5)_3F_3]^-$, $[P(CF_3)_3F_3]^-$, $[P(C_2F_4H)(CF_3)_2F_3]^-$, $[P(C_2F_3H_2)_3F_3]^-$, $[P(C_2F_5)(CF_3)_2F_3]^-$, $[P(C_3F_7)_3 F_3]^-$, $[P(C_4F_9)_3F_3]^-$ and $[P(C_2F_5)_2F_4]^-$.

In the said salts (II), $R^{1'}$ to $R^{4'}$ is preferably selected from hydrogen, straight-chain or branched alkyl having 1-20 C atoms, dialkylamino containing alkyl groups having 1-4 C atoms, which, however, is not bonded to the heteroatom of the heterocycle, and where, in the substituents $R^{1'}$ to $R^{4'}$, one or two non-adjacent carbon atoms which are not bonded directly to the heteroatom may be replaced by atoms and/or atom groups selected from the group —O—, —S—, —S(O)—, —$SO_2$— and —NR'— or by the end group CN, —C(O)X' or —$SO_2$X', where R'=H, non-, partially or perfluorinated $C_1$- to $C_3$-alkyl, $C_3$- to $C_7$-cycloalkyl, unsubstituted or substituted phenyl, or an unsubstituted or substituted heterocycle, and X'=OH, F, Cl or Br. Examples of the said substituents have already been mentioned above. In the said salts (II), $R^{1'}$ to $R^{4'}$ is particularly preferably selected from hydrogen, straight-chain or branched alkyl having 1-20 C atoms or alkoxyalkyl, in which alkoxy denotes $C_1$-$C_8$-alkoxy and alkyl denotes $C_1$-$C_8$-alkyl.

The salts (II) are very particularly preferably those having pyrrolidinium, piperidinium and morpholinium cations.

The present invention furthermore relates to salts (III) having cations selected from the group comprising

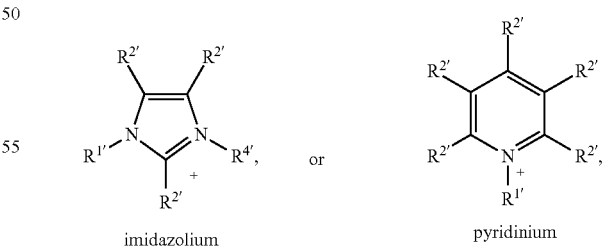

imidazolium            pyridinium where the substituents
$R^{1'}$ to $R^{4'}$ each, independently of one another, have the meaning straight-chain or branched alkyl having 1-20 C atoms, with the proviso that at least one of the substituents $R^{1'}$ or $R^{4'}$ is straight-chain or branched alkyl having 9-20 C atoms,
straight-chain or branched alkenyl having 2-20 C atoms and one or more double bonds, straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms where the substituents $R^{1'}$ and $R^{4'}$ may be partially or fully substituted by F, but where $R^{1'}$ and $R^{4'}$ cannot simultaneously be fully substituted by F, where the substituents $R^{2'}$ and $R^{3'}$ may be partially or fully substituted by OR', N(R')$_2$, CN or halogen and where, in $R^{1'}$ to $R^{4'}$, one or two non-adjacent carbon atoms which are not in the α-position to the heteroatom may be replaced by atoms and/or atom groups selected from the group —O—, —S—, —SO$_2$— and —NR'— or by the end group CN, —C(O)X' or —SO$_2$X', where R'=H, non-, partially or perfluorinated C$_1$- to C$_6$-alkyl, C$_3$- to C$_7$-cycloalkyl, unsubstituted or substituted phenyl, or an unsubstituted or substituted heterocycle, and X'=OH, F, Cl or Br, and anions selected from the group of $[PF_x(C_yF_{2y+1-z}H_z)_{6-x}]^-$ anions, where $2 \leq x \leq 5$, $1 \leq y \leq 8$ and $0 \leq z \leq 2y+1$, where 3-methyl-1-octadecylimidazolium tris(pentafluoroethyl)trifluorophosphate is excluded.

The anion of the salts (III) is preferably selected from the group comprising $[P(C_2F_5)_3F_3]^-$, $[P(CF_3)_3F_3]^-$, $[P(C_2F_4H)(CF_3)_2F_3]^-$, $[P(C_2F_3H_2)_3F_3]^-$, $[P(C_2F_5)(CF_3)_2F_3]^-$, $[P(C_3F_7)_3F_3]^-$, $[P(C_4F_9)_3F_3]^-$, and $[P(C_2F_5)_2F_4]^-$.

In the said salts (III), $R^{1'}$ to $R^{4'}$ is preferably selected from straight-chain or branched alkyl having 1-20 C atoms, with the proviso that at least one of the substituents $R^{1'}$ or $R^{4'}$ is straight-chain or branched alkyl having 9-20 C atoms, where the substituents $R^{2'}$ and $R^{3'}$ may be partially or fully substituted by OR', N(R')$_2$, CN or halogen and where, in $R^{1'}$ to $R^{4'}$, one or two non-adjacent carbon atoms which are not in the α-position to the heteroatom may be replaced by atoms and/or atom groups selected from the group —O—, —S—, —SO$_2$— and —NR'— or by the end group CN, —C(O)X' or —SO$_2$X', where R'=H, non-, partially or perfluorinated C$_1$- to C$_6$-alkyl, C$_3$- to C$_7$-cycloalkyl, unsubstituted or substituted phenyl, or an unsubstituted or substituted heterocycle, and X'=OH, F, Cl or Br. $R^{1'}$ to $R^{4'}$ is preferably selected from straight-chain or branched alkyl having 1-20 C atoms, with the proviso that at least one of the substituents $R^{1'}$ or $R^{4'}$ is straight-chain or branched alkyl having 9-20 C atoms.

The salts (III) are very particularly preferably compounds having imidazolium cations in which $R^{1'}$ denotes straight-chain or branched alkyl having 1-8 C atoms and $R^{4'}$ denotes straight-chain or branched alkyl having 9-20 C atoms. The salts (III) are likewise particularly preferably compounds having pyridinium cations in which $R^{1'}$ denotes straight-chain or branched alkyl having 9-20 C atoms and $R^{2'}$ denotes straight-chain or branched alkyl having 1-8 C atoms.

The said salts (I), (II) and (III) or the mixture thereof are particularly suitable as solvent or solvent additive, as phase-transfer catalyst, as extractant, as heat-transfer medium, as surface-active substance, as plasticiser, as flameproofing agent and/or as conductive salt for electrochemical cells. The salts of the formula (I) are, in addition, particularly suitable as cyanilation reagents for organic substrates. For the purposes of the present invention, organic substrates are taken to mean all organic compounds into which a cyano group can be introduced by means of the salts (I). These can be simple chemical structures, but also complex biochemically relevant compounds, such as, for example, proteins, carbohydrates, polypeptides, RNA, DNA, etc., which can be activated for further reactions with the aid of these cyanilation reagents.

The corresponding uses and the performance of these reactions are known to the person skilled in the art. In the said cyanilation reactions, the salts (I) according to the invention have the advantage that they are more stable than the N-cyano-3-(dimethylamino)pyridinium tetrafluoroborate currently employed. Since the said salts have different mixing properties, with, for example, solvents, the reaction conditions for the cyanilation reaction can be adapted in accordance with needs. The process management for carrying out the reaction can thus be simplified for the user through the use of the salts according to the invention.

Even without further comments, it is assumed that a person skilled in the art will be able to utilise the above description in the broadest scope. The preferred embodiments and examples should therefore merely be regarded as descriptive disclosure which is absolutely not limiting in any way.

It goes without saying to the person skilled in the art that substituents, such as, for example, H, N, O, Cl, F, in the compounds mentioned above and below may be replaced by the corresponding isotopes.

The $^1$H-, $^{19}$F- and $^{31}$P-NMR spectra are measured on a Bruker Avance 250 spectrometer (250.13 MHz for $^1$H, 235.36 for $^{19}$F and 101.25 for $^{31}$P) in acetonitrile-D$_3$, unless indicated otherwise in the examples. CCl$_3$F and TMS are employed as internal reference in the measurement of the $^{19}$F NMR and proton NMR spectra. For the $^{31}$P NMR spectra, 85% H$_3$PO$_4$ in D$_2$O in acetonitrile-D$_3$ is measured as external reference at a frequency of 230.11 Hz in a separate experiment.

EXAMPLES

Example 1

Triethyloxonium tris(pentafluoroethyl)trifluorophosphate

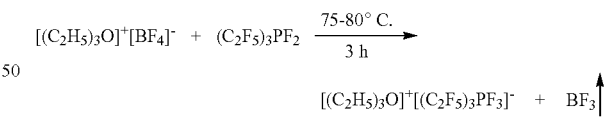

A mixture of 5.2 g (27.37 mmol) of triethyloxonium tetrafluoroborate and 12.8 g (30.05 mmol) of tris(pentafluoroethyl)difluorophosphorane is heated to 75-80° C. (temperature of the oil bath) and stirred for three hours under a nitrogen atmosphere. Volatile constituents are pumped off over the course of one hour under reduced pressure (7 Pa) at 75-80° C. (temperature of the oil bath), giving 14.7 g of a solid. The yield of triethyloxonium tris(pentafluoroethyl)trifluorophosphate is 98.0%, calculated according to the triethyloxonium tetrafluoroborate employed. The product is investigated by NMR spectroscopy.

$^1$H NMR spectrum, ppm: 1.52 t (3CH$_3$), 4.66 q (3CH$_2$); $J^3_{H,H}$=7.1 Hz.

$^{19}$F NMR spectrum, ppm: −43.57 dm (PF), −79.62 m (CF$_3$), −81.30 m (2CF$_3$), −87.04 dm (PF$_2$), −115.01 dm (CF$_2$), −115.56 dm (2CF$_2$); $J^1_{P,F}$=889 Hz, $J^1_{P,F}$=906 Hz, $J^2_{P,F}$=86 Hz, $J^2_{P,F}$=107 Hz.

Example 2

Triethylsulfonium tris(pentafluoroethyl)trifluorophosphate

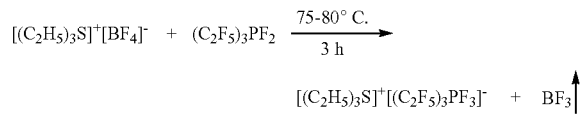

A mixture of 3.0 g (14.56 mmol) of triethylsulfonium tetrafluoroborate and 6.8 g (15.97 mmol) of tris(pentafluoroethyl)difluorophosphorane is heated to 75-80° C. (temperature of the oil bath) and stirred for three hours under a nitrogen atmosphere. Volatile constituents are pumped off over the course of one hour under reduced pressure (7 Pa) at 75-80° C. (temperature of the oil bath), giving 14.7 g of a solid. The yield of triethylsulfonium tris(pentafluoroethyl)trifluorophosphate is 97.4%, calculated according to triethylsulfonium tetrafluoroborate employed. The product is investigated by NMR spectroscopy.

$^1$H NMR spectrum, ppm: 1.40 t (3CH$_3$), 3.21 q (3CH$_2$); $J^3_{H,H}$=7.4 Hz.

$^{19}$F NMR spectrum, ppm: −43.62 dm (PF), −79.67 m (CF$_3$), −81.36 m (2CF$_3$), −87.03 dm (PF$_2$), −115.09 dm (CF$_2$), −115.62 dm (2CF$_2$); $J^1_{P,F}$=889 Hz, $J^1_{P,F}$=906 Hz, $J^2_{P,F}$=84 Hz, $J^2_{P,F}$=105 Hz.

$^{31}$P NMR spectrum, ppm: −149.0 d, t, m.

Example 3

Triethyloxonium bis(trifluoromethylsulfonyl)imide

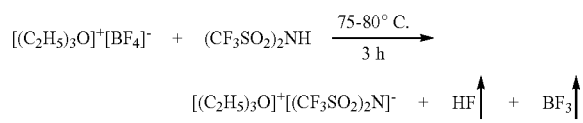

A mixture of 3.7 g (19.47 mmol) of triethyloxonium tetrafluoroborate and 5.47 g (19.46 mmol) of bis(trifluoromethylsulfonyl)imide is heated to 75-80° C. (temperature of the oil bath) and stirred for three hours under a nitrogen atmosphere. Volatile constituents are pumped off over the course of one hour under reduced pressure (7 Pa) at 75-80° C. (temperature of the oil bath), giving 7.46 g of an oil. The yield of triethyloxonium bis(trifluoromethylsulfonyl)imide is virtually quantitative. The product was investigated by NMR spectroscopy.

$^1$H NMR spectrum, ppm: 1.51 t (3CH$_3$), 4.68 q (3CH$_2$); $J^3_{H,H}$=7.1 Hz.

$^{19}$F NMR spectrum, ppm: −78.98 s

Example 4

Triethylsulfonium bis(trifluoromethylsulfonyl)imide

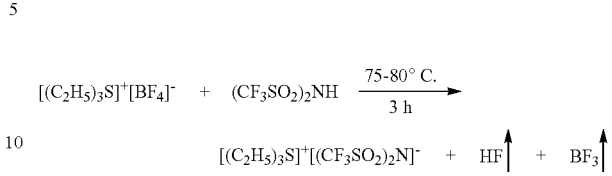

A mixture of 2.82 g (13.69 mmol) of triethylsulfonium tetrafluoroborate and 3.85 g (13.69 mmol) of bis(trifluoromethylsulfonyl)imide is heated to 75-80° C. (temperature of the oil bath) and stirred for three hours under a nitrogen atmosphere. Volatile constituents are pumped off over the course of one hour under reduced pressure (7 Pa) at 75-80° C. (temperature of the oil bath), giving 5.35 g of a solid. The yield of triethylsulfonium bis(trifluoromethylsulfonyl)imide is 97.9%. The product is investigated by NMR spectroscopy.

$^1$H NMR spectrum, ppm: 1.39 t (3CH$_3$), 3.22 q (3CH$_2$); $J^3_{H,H}$=7.4 Hz.

$^{19}$F NMR spectrum, ppm: −78.89 s (CF$_3$).

Example 5

Triethyloxonium tetracyanoborate

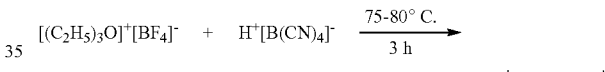

A mixture of 1.00 g (5.26 mmol) of triethyloxonium tetrafluoroborate and 1.195 g (5.26 mmol) of a complex of tetracyanoboric acid with diethyl ether, H[B(CN)$_4$].1.5 Et$_2$O, is heated to 75-80° C. (temperature of the oil bath) and stirred for three hours under a nitrogen atmosphere. Volatile constituents are pumped off over the course of one hour under reduced pressure (7 Pa) at 75-80° C. (temperature of the oil bath), giving 0.98 g of an oil, The yield of triethyloxonium tetracyanoborate is 85.4%. The product is investigated by NMR spectroscopy.

$^1$H NMR spectrum, ppm: 1.51 t (3CH$_3$), 4.68 q (3CH$_2$); $J^3_{H,H}$=7.1 Hz.

$^{11}$B NMR spectrum, (solvent: acetonitrile-D$_3$; reference: BF$_3$-etherate external) ppm: −38.6 s.

Example 6

Triethylsulfonium pentafluoroethyltrifluoroborate

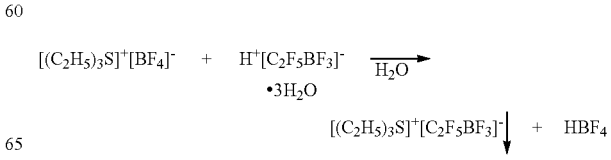

1.3 g (5.34 mmol) of pentafluoroethyltrifluoroboric acid trihydrate, H[C$_2$F$_5$BF$_3$].3H$_2$O, is added to a solution of 1.0 g (4.85 mmol) of triethylsulfonium tetrafluoroborate in 10 ml of ice-water with stirring. The suspension is immediately extracted with dichloromethane (3×20 ml), and the resultant solution is dried using magnesium sulfate. After MgSO$_4$ has been filtered off, the dichloromethane is removed in vacuo (7 Pa) at room temperature, and the residue is dried in vacuo for a further three hours, giving 1.24 g of a slightly yellowish oil. The yield of triethylsulfonium pentafluoroethyltrifluoroborate is 83.5%, calculated according to the triethylsulfonium tetrafluoroborate employed. The product is investigated by NMR spectroscopy.

$^1$H NMR spectrum, ppm: 1.39 t (3CH$_3$), 3.22 q (3CH$_2$); J$^3_{H,H}$=7.5 Hz.

$^{19}$F NMR spectrum, ppm: −83.17 q (CF$_3$), −136.00 q (CF$_2$), −152.83 q, q (BF$_3$); J$^1_{B,F}$=40.7 Hz, J$^2_{B,F}$=19.6 Hz, J$^4_{F,F}$=5.0 Hz.

$^{11}$B NMR spectrum, (reference: BF$_3$-etherate external) ppm: −0.61 q, t; J$^1_{B,F}$=40.7H$_z$, J$^2_{B,F}$=20.4 Hz.

Example 7

Triethylsulfonium pentafluoroethyltrifluoroborate

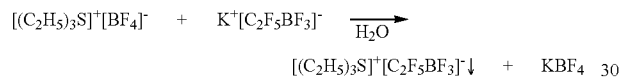

A solution of 1.03 g (4.56 mmol) of potassium pentafluoroethyltrifluoroborate, K[C$_2$F$_5$BF$_3$], in 10 ml of ice-water is added to a solution of 0.87 g (4.22 mmol) of triethylsulfonium tetrafluoroborate in 5 ml of ice-water with stirring. The suspension is immediately extracted with dichloromethane (3×20 ml), and the resultant solution is dried using magnesium sulfate. After MgSO$_4$ has been filtered off, the dichloromethane is removed in vacuo (7 Pa) at room temperature, and the residue is dried in vacuo for a further three hours, giving 1.11 g of a slightly yellowish oil. The yield of triethylsulfonium pentafluoroethyltrifluoroborate is 85.9%, calculated according to the triethylsulfonium tetrafluoroborate employed. The product is investigated by NMR spectroscopy. The spectra correspond to those from Example 7.

Example 8

Triethyloxonium tris(pentafluoroethyl)trifluorophosphate

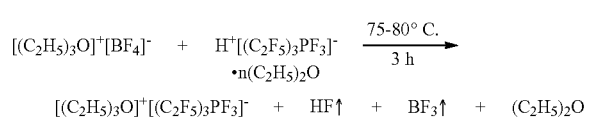

A mixture of 1.00 g (5.26 mmol) of triethyloxonium tetrafluoroborate and 2.35 g (5.27 mmol) of tris(pentafluoroethyl)trifluorophosphoric acid in 2.8 cm$^3$ of diethyl ether is heated to 75-80° C. (temperature of the oil bath) and stirred for three hours under a nitrogen atmosphere. Volatile constituents are pumped off over the course of one hour under reduced pressure (7 Pa) at 75-80° C. (temperature of the oil bath), giving 2.76 g of an oil. The yield of triethyloxonium tris(pentafluoroethyl)trifluorophosphate is 95.7%. The product is investigated by NMR spectroscopy.

$^1$H NMR spectrum, ppm: 1.51 t (3CH$_3$), 4.68 q (3CH$_2$); J$^3_{H,H}$=7.1 Hz.

$^{19}$F NMR spectrum, ppm: −43.59 dm (PF), −79.64 m (CF$_3$), −81.33 m (2CF$_3$), −87.07 dm (PF$_2$), −115.08 dm (CF$_2$), −115.59 dm (2CF$_2$); J$^1_{P,F}$=889 Hz, J$^1_{P,F}$=905 Hz, J$^2_{P,F}$=83 Hz, J$^2_{P,F}$=107 Hz.

Example 9

1-Cyano-4-dimethylaminopyridinium tris(pentafluoroethyl)trifluorophosphate

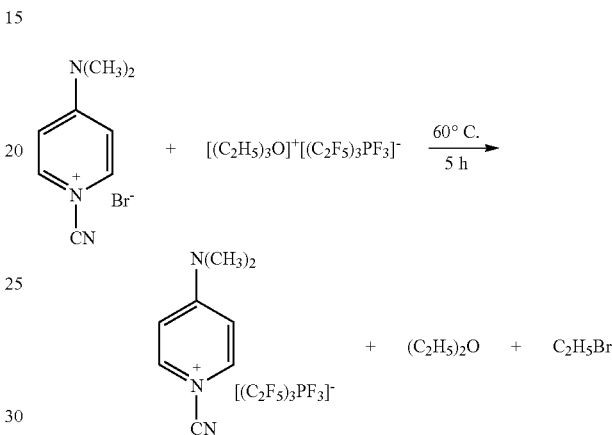

A mixture of 5.93 g (25.90 mmol) of 1-cyano-4-dimethylaminopyridinium bromide and 14.30 g (26.09 mmol) of triethyloxonium tris(pentafluoroethyl)trifluorophosphate from Example 1 is heated to 60° C. (temperature of the oil bath) and stirred for five hours under a nitrogen atmosphere. Volatile constituents are pumped off over the course of one hour under reduced pressure (7 Pa) at 50° C. (temperature of the oil bath), giving 14.32 g of a solid. The yield of 1-cyano-4-dimethylaminopyridinium tris(pentafluoroethyl)trifluorophosphate is 93.2%, based on the 1-cyano-4-dimethylaminopyridinium bromide employed. The product is investigated by NMR spectroscopy.

$^1$H NMR spectrum, ppm: 3.34 s (2CH$_3$), 6.99 d (CH), 7.03 d (CH), 8.04 d (CH), 8.20 d (CH); J$^3_{H,H}$=8.2 Hz.

$^{19}$F NMR spectrum, ppm: −43.57 dm (PF), −79.60 m (CF$_3$), −81.30 m (2CF$_3$), −87.00 dm (PF$_2$), −115.05 dm (CF$_2$), −115.60 dm (2CF$_2$); J$^1_{P,F}$=889 Hz, J$^1_{P,F}$=906 Hz, J$^2_{P,F}$=81 Hz, J$^2_{P,F}$=107 Hz.

Example 10

1-Ethyl-3-methylimidazolium tris(pentafluoroethyl)trifluorophosphate

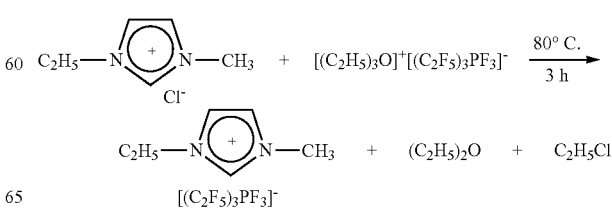

A mixture of 1.12 g (7.64 mmol) of 1-ethyl-3-methylimidazolium chloride and 4.19 g (7.64 mmol) of triethyloxonium tris(pentafluoroethyl)trifluorophosphate from Example 1 is heated to 70-80° C. (temperature of the oil bath) and stirred for three hours under a nitrogen atmosphere. Volatile constituents are pumped off over the course of one hour under reduced pressure (7 Pa) at 70° C. (temperature of the oil bath), giving 4.20 g of a liquid. The yield of 1-ethyl-3-methylimidazolium tris(pentafluoroethyl)trifluorophosphate is 98.9%, based on the 1-ethyl-3-methylimidazolium chloride employed. The product is investigated by NMR spectroscopy.

$^1$H NMR spectrum, ppm: 1.47 t (CH$_3$), 3.84 s (CH$_3$), 4.18 q (CH$_2$), 7.34 m (CH), 7.39 m (CH), 8.43 br. s. (CH); $J^3_{H,H}$=7.3 Hz.

$^{19}$F NMR spectrum, ppm: −43.54 dm (PF), −79.60 m (CF$_3$), −81.29 m (2CF$_3$), −86.96 dm (PF$_2$), −115.03 dm (CF$_2$), −115.55 dm (2CF$_2$); $J^1_{P,F}$=889 Hz, $J^1_{P,F}$=906 Hz, $J^2_{P,F}$=84 Hz, $J^2_{P,F}$=106 Hz.

$^{31}$P NMR spectrum, ppm: −149.0 d, t, m.

Example 11

1-Ethyl-3-methylimidazolium tris(pentafluoroethyl)trifluorophosphate

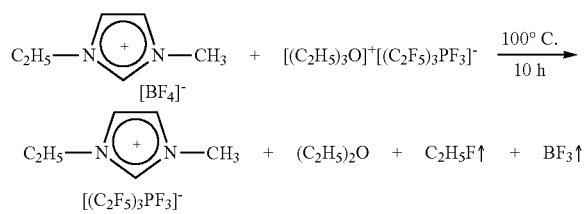

A mixture of 0.54 g (2.73 mmol) of 1-ethyl-3-methylimidazolium tetrafluoroborate and 1.50 g (2.74 mmol) of triethyloxonium tris(pentafluoroethyl)trifluorophosphate from Example 1 is heated to 100° C. (temperature of the oil bath) and stirred for ten hours under a nitrogen atmosphere. Volatile constituents are pumped off over the course of one hour under reduced pressure (7 Pa) at 100° C. (temperature of the oil bath), giving 1.37 g of a liquid. The yield of 1-ethyl-3-methylimidazolium tris(pentafluoroethyl)trifluorophosphate is 90.3%, based on the 1-ethyl-3-methylimidazolium tetrafluoroborate employed. The product is investigated by NMR spectroscopy.

NMR data: see Example 10

Example 12

1-Ethyl-3-methylimidazolium tris(pentafluoroethyl)trifluorophosphate

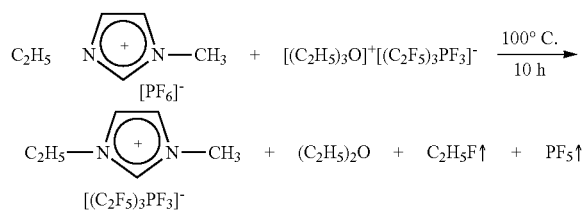

A mixture of 1.73 g (6.75 mmol) of 1-ethyl-3-methylimidazolium hexafluorophosphate and 3.70 g (6.75 mmol) of triethyloxonium tris(pentafluoroethyl)trifluorophosphate from Example 1 is heated to 100° C. (temperature of the oil bath) and stirred for ten hours under a nitrogen atmosphere. The volatile constituents are pumped off over the course of one hour under reduced pressure (7 Pa) at 100° C. (temperature of the oil bath), giving 3.71 g of a liquid. The yield of 1-ethyl-3-methylimidazolium tris(pentafluoroethyl)trifluorophosphate is 98.7%, based on the 1-ethyl-3-methylimidazolium hexafluorophosphate employed. The product is investigated by NMR spectroscopy.

NMR data: see Example 10

Example 13

Hexamethylguanidinium tris(pentafluoroethyl)trifluorophosphate

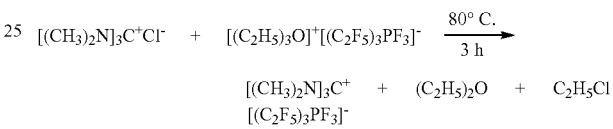

A mixture of 1.81 g (10.07 mmol) of hexamethylguanidinium chloride and 5.53 g (10.09 mmol) of triethyloxonium tris(pentafluoroethyl)trifluorophosphate from Example 1 is heated to 70-80° C. (temperature of the oil bath) and stirred for three hours under a nitrogen atmosphere. Volatile constituents are pumped off over the course of one hour under reduced pressure (7 Pa) at 70° C. (temperature of the oil bath), giving 5.88 g of a solid. The yield of hexamethylguanidinium tris(pentafluoroethyl)trifluorophosphate is 98.9%, based on the hexamethylguanidinium chloride employed. The product is investigated by NMR spectroscopy.

$^1$H NMR spectrum, ppm: 2.89 s (6CH$_3$).

$^{19}$F NMR spectrum, ppm: −43.63 dm (PF), −79.68 m (CF$_3$), −81.37 m (2CF$_3$), −87.05 dm (PF$_2$), −115.07 dm (CF$_2$), −115.64 dm (2CF$_2$); $J^1_{P,F}$=891 Hz, $J^1_{P,F}$=906 Hz, $J^2_{P,F}$=84 Hz, $J^2_{P,F}$=105 Hz.

$^{31}$P NMR spectrum, ppm: −149.0 d, t, m.

Example 14

1-Cyano-4-dimethylaminopyridinium bis(trifluoromethylsulfonyl)imide

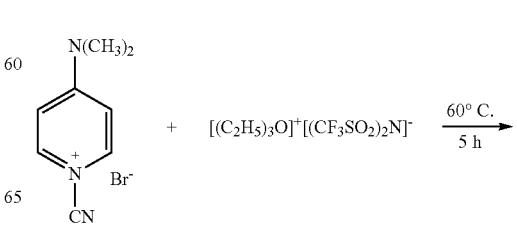

-continued

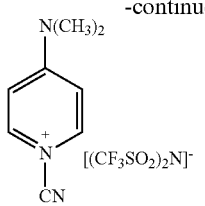
+ (C₂H₅)₂O + C₂H₅Br

A mixture of 5.22 g (22.89 mmol) of 1-cyano-4-dimethylaminopyridinium bromide and 8.77 g (22.88 mmol) of triethyloxonium bis(trifluoromethylsulfonyl)imide from Example 3 is heated to 60° C. (temperature of the oil bath) and stirred for five hours under a nitrogen atmosphere. Volatile constituents are pumped off over the course of one hour under reduced pressure (7 Pa) at 50° C. (temperature of the oil bath), giving 14.32 g of a solid. The yield of 1-cyano-4-dimethylaminopyridinium bis(trifluoromethylsulfonyl)imide is 98.2%, based on the 1-cyano-4-dimethylaminopyridinium bromide employed. The product is investigated by NMR spectroscopy.

¹H NMR spectrum, ppm: 3.34 s (2CH₃), 6.99 d (CH), 7.03 d (CH), 8.04 d (CH), 8.19 d (CH); $J^3_{H,H}$=8.2 Hz.

¹⁹F NMR spectrum, ppm: −78.96 s.

Example 15

1-Ethyl-3-methylimidazolium bis(trifluoromethylsulfonyl)imide

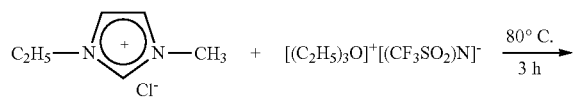

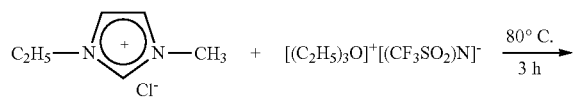

A mixture of 1.32 g (9.0 mmol) of 1-ethyl-3-methylimidazolium chloride and 3.45 g (9.0 mmol) of triethyloxonium bis(trifluoromethylsulfonyl)imide from Example 3 is heated to 70-80° C. (temperature of the oil bath) and stirred for four hours under a nitrogen atmosphere. Volatile constituents are pumped off over the course of one hour under reduced pressure (7 Pa) at 70° C. (temperature of the oil bath), giving 3.45 g of a liquid. The yield of 1-ethyl-3-methylimidazolium bis(trifluoromethylsulfonyl)imide is 97.9%, based on the 1-ethyl-3-methylimidazolium chloride employed. The product is investigated by NMR spectroscopy.

¹H NMR spectrum, ppm: 1.45 t (CH₃); 3.83 s (CH₃); 4.17 q (CH₂); 7.37 m (CH); 7.43 m (CH); 8.57 br. s. (CH); $J^3_{H,H}$=7.3 Hz.

¹⁹F NMR spectrum, ppm: −78.91 s (CF₃).

Example 16

1-Ethyl-3-methylimidazolium tris(pentafluoroethyl)trifluorophosphate

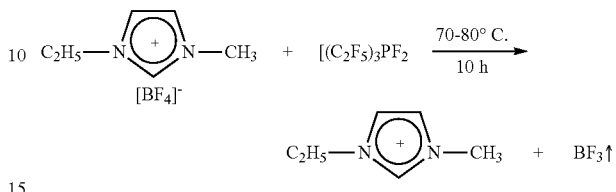

A mixture of 0.47 g (2.37 mmol) of 1-ethyl-3-methylimidazolium tetrafluoroborate and 1.12 g (2.63 mmol) of tris(pentafluoroethyl)difluorophosphorane is heated to 70-80° C. (temperature of the oil bath) and stirred for 10 hours under a nitrogen atmosphere. Volatile constituents are pumped off over the course of one hour under reduced pressure (7 Pa) at 70° C. (temperature of the oil bath), giving 1.30 g of a liquid. The yield of 1-ethyl-3-methylimidazolium tris(pentafluoroethyl)trifluorophosphate is 98.5%, based on the 1-ethyl-3-methylimidazolium tetrafluoroborate employed. The product is investigated by NMR spectroscopy.

NMR data: see Example 10

Example 17

1-Ethyl-3-methylimidazolium tris(pentafluoroethyl)trifluorophosphate

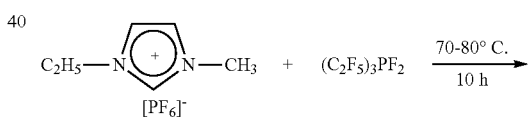

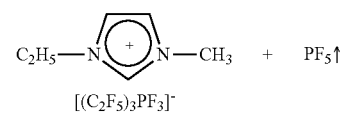

A mixture of 2.34 g (9.14 mmol) of 1-ethyl-3-methylimidazolium hexafluorophosphate and 4.28 g (10.05 mmol) of tris(pentafluoroethyl)difluorophosphorane is heated to 70-80° C. (temperature of the oil bath) and stirred for 10 hours under a nitrogen atmosphere. Volatile constituents are pumped off over the course of one hour under reduced pressure (7 Pa) at 70° C. (temperature of the oil bath), giving 4.95 g of a liquid. The yield of 1-ethyl-3-methylimidazolium tris(pentafluoroethyl)trifluorophosphate is 97.4%, based on the 1-ethyl-3-methylimidazolium hexafluorophosphate employed. The product is investigated by NMR spectroscopy.

NMR data: see Example 10

Example 18

Tritylium tris(pentafluoroethyl)trifluorophosphate

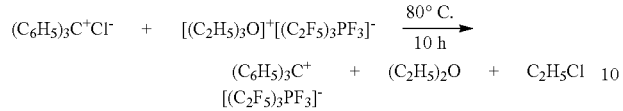

A mixture of 1.12 g (4.02 mmol) of tritylium chloride and 2.20 g (4.02 mmol) of triethyloxonium tris(pentafluoroethyl)trifluorophosphate from Example 1 is heated to 70-80° C. (temperature of the oil bath) and stirred for ten hours under a nitrogen atmosphere. Volatile constituents are pumped off over the course of one hour under reduced pressure (7 Pa) at 70° C. (temperature of the oil bath), giving 2.59 g of a solid. The yield of tritylium tris(pentafluoroethyl)trifluorophosphate is 93.6%. The product is investigated by NMR spectroscopy.

$^1$H NMR spectrum, ppm: 7.18-740 m (3C$_6$H$_5$);

$^{19}$F NMR spectrum, ppm: −43.65 dm (PF), −79.69 m (CF$_3$), −81.39 m (2CF$_3$), −87.07 dm (PF$_2$), −115.14 dm (CF$_2$), −115.68 dm (2CF$_2$); J$^1_{P,F}$=891 Hz, J$^1_{P,F}$=902 Hz, J$^2_{P,F}$=87 Hz, J$^2_{P,F}$=105 Hz.

Example 19

1-Decyl-3-methylimidazolium tris(pentafluoroethyl)trifluorophosphate

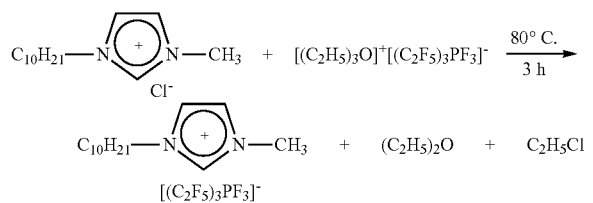

A mixture of 0.34 g (1.31 mmol) of 1-decyl-3-methylimidazolium chloride and 0.72 g (1.31 mmol) of triethyloxonium tris(pentafluoroethyl)trifluorophosphate from Example 1 is heated to 80° C. (temperature of the oil bath) and stirred for three hours under a nitrogen atmosphere. Volatile constituents are pumped off over the course of one hour under reduced pressure (7 Pa) at 80° C. (temperature of the oil bath), giving 0.84 g of a liquid. The yield of 1-decyl-3-methylimidazolium tris(pentafluoroethyl)trifluorophosphate is 96%. The product is investigated by NMR spectroscopy.

$^1$H NMR spectrum, ppm: 0.90 m (CH$_3$), 1.30 m (7CH$_2$), 1.82 m (CH$_2$), 3.82 s (CH$_3$), 4.11 t (CH$_2$), 7.32 d, d (CH), 7.36 d, d (CH), 8.37 m (CH); J$^3_{H,H}$=7.4 Hz, J$^4_{H,H}$=1.8 Hz.

$^{19}$F NMR spectrum, ppm: −43.61 dm (PF), −79.65 m (CF$_3$), −81.34 m (2CF$_3$), −87.07 dm (PF$_2$), −115.09 dm (CF$_2$), −115.61 dm (2CF$_2$); J$^1_{P,F}$=891 Hz, J$^1_{P,F}$=906 Hz, J$^2_{P,F}$=83 Hz, J$^2_{P,F}$=105 Hz.

$^{31}$P NMR spectrum, ppm: −148.1 d, t, m.

Example 20

1-Hexyl-1-methylpyrrolidinium tris(pentafluoroethyl)trifluorophosphate

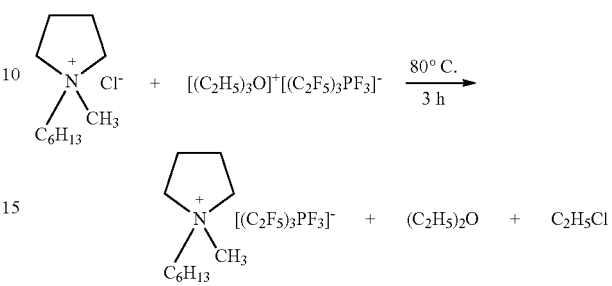

A mixture of 0.20 g (0.97 mmol) of 1-hexyl-1-methylpyrrolidinium chloride and 0.53 g (0.97 mmol) of triethyloxonium tris(pentafluoroethyl)trifluorophosphate from Example 1 is heated to 80° C. (temperature of the oil bath) and stirred for three hours under a nitrogen atmosphere. Volatile constituents are pumped off over the course of one hour under reduced pressure (7 Pa) at 80° C. (temperature of the oil bath), giving 0.55 g of a liquid. The yield of 1-hexyl-1-methylpyrrolidinium tris(pentafluoroethyl)trifluorophosphate is 93%. The product is investigated by NMR spectroscopy.

$^1$H NMR spectrum, ppm: 0.92 m (CH$_3$), 1.35 m (3CH$_2$), 1.74 m (CH$_2$), 2.16 m (2CH$_2$), 2.93 s (CH$_3$), 3.18 m (CH$_2$), 3.40 m (2CH$_2$).

$^{19}$F NMR spectrum, ppm: −43.58 dm (PF), −79.64 m (CF$_3$), −81.34 m (2CF$_3$), −87.00 dm (PF$_2$), −115.03 dm (CF$_2$), −115.58 dm (2CF$_2$); J$^1_{P,F}$=891 Hz, J$^1_{P,F}$=906 Hz, J$^2_{P,F}$=84 Hz, J$^2_{P,F}$=106 Hz.

$^{31}$P NMR spectrum, ppm: −148.1 d, t, m.

Alternative compounds mentioned within the present invention can be prepared analogously in a manner which is obvious to the person skilled in the art.

The invention claimed is:

1. An Oxonium salt having [(R°)$_3$O]$^+$ cations or sulfonium salt having [(R°)$_3$S]$^+$ cations,
where R° denotes straight-chain or branched alkyl group having 1-8 C atoms or unsubstituted phenyl or phenyl which is substituted by R°, OR°, N(R°)$_2$, CN or halogen, and for the oxonium salt
anions selected from the group consisting of [PF$_x$(C$_y$F$_{2y+1-z}$H$_z$)$_{6-x}$]$^-$ anions, where 2<x<5, 1<y<8 and 0<z<2y+1,
or anions selected from the group consisting of [(BF$_n$(CN)$_{4-n}$]$^-$ anions, where n=0, 1, 2 or 3,
or anions selected from the group consisting of [(R$^{f1}$SO$_2$)$_2$N]$^-$ anions, where R$^{f1}$ denotes F or perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups,
or anions selected from the group consisting of [BF$_w$R$^{f2}_{4-w}$]$^-$ anions, where w=0, 1, 2 or 3, where R$^{f2}$ denotes perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups, where $R^{f1}$ or $R^{f2}$ may in each case be identical or different, where a pair of $R^{f1}$ or a pair of $R^{f2}$ may be connected to one another by single or double bonds, and where, in $R^{f1}$ or $R^{f2}$, one or two non-adjacent carbon atoms of which are not in the α-position to the heteroatom may be replaced by atoms and/or atom groups selected from the group consisting of —O—, —SO$_2$— and —NR'— or by the end group —SO$_2$X', where R'=non-, partially- or perfluorinated $C_1$- to $C_6$-alkyl, $C_3$- to $C_7$-cycloalkyl, unsubstituted or substituted phenyl, or an unsubstituted or substituted heterocycle, and X'=F, Cl or Br, and for the sulfonium salt anions selected from the group consisting of $[(BF_n(CN)_{4-n}]^-$ anions, where n=0, 1, 2 or 3.

2. An oxonium salt or sulfonium salt according to claim 1, wherein the anions for the oxonium salt are $[(CF_3SO_2)_2N]^-$, $[(C_2F_5SO_2)_2N]^-$, $[(FSO_2)_2N]^-$, $[P(C_2F_5)_3F_3]^-$, $[P(CF_3)_3F_3]^-$, $[P(C_2F_4H)(CF_3)_2F_3]^-$, $[P(C_2F_3H_2)_3F_3]^-$, $[P(C_2F_5)(CF_3)_2F_3]^-$, $[P(C_3F_7)_3F_3]^-$, $[P(C_4F_9)_3F_3]^-$, $[P(C_2F_5)_2F_4]^-$, $[BF_3(CF_3)]^-$, $[BF_2(C_2F_5)_2]^-$, $[BF_3(C_2F_5)]^-$, $[BF_2(CF_3)_2]^-$, $[B(C_2F_5)_4]^-$, $[BF_3(CN)]^-$, $[BF_2(CN)_2]^-$, $[B(CN)_4]^-$, or $[B(CF_3)_4]^-$ anions, and for the sulfonium salt are $[BF_3(CN)]^-$, $[BF_2(CN)_2]^-$, or $[B(CN)_4]^-$ anions.

3. An oxonium salt or sulfonium salt according to claim 1, wherein the $[(R^o)_3O]^+$ cation is a $[(C_2H_5)_3O]^+$ cation or the $[(R^o)_3S]^+$ cation is a $[(C_2H_5)_3S]^+$ cation.

4. A process for preparing an oxonium salt according to claim 1 having $[PF_x(C_yF_{2y+1-z}H_z)_{6-x}]^-$ anions comprising reacting a $[(R^o)_3O]^+$ tetrafluoroborate or hexafluorophosphate with a phosphorane of formula $PF_a(C_yF_{2y+1-z}H_z)_{5-a}$, where 1<a<4, and $R^o$, y and z have the meaning indicated for the oxonium salt.

5. A process according to claim 4, wherein the reaction is carried out without addition of a solvent.

6. A process according to claim 4, wherein the reaction is carried out at temperatures of 0° C. to 150° C.

7. A process for preparing an oxonium salt or sulfonium salt according to claim 1, comprising, for the oxonium salt, reacting an $[(R^o)_3O]^+$ tetrafluoroborate or hexafluorophosphate with $H^+[PF_x(C_yF_{2y+1-z}H_z)_{6-x}]^-$, $H^+[BF_n(CN)_{4-n}]^-$, $H^+[R^{f1}SO_2)_2N]^-$ or $H^+[BF_wR^{f2}_{4-w}]^-$ or with an alkali metal salt or alkaline-earth metal salt of $H^+[PF_x(C_yF_{2y+1-z}H_z)_{6-x}]^-$, $H^+[BF_n(CN)_{4-n}]^-$, $H^+[R^{f1}SO_2)_2N]^-$ or $H^+[BF_wR^{f2}_{4-w}]^-$, or comprising, for the sulfonuim salt, reacting an $[(R^o)_3S]^+$ tetrafluoroborate or hexafluorophosphate-with $H^+[BF_n(CN)_{4-n}]^-$, or with an alkali metal salt or alkaline-earth metal salt of $H^+[BF_n(CN)_{4-n}]^-$, where $R^o$, x, y, z, n, $R^{f1}$, $R^{f2}$ and w have the meaning indicated for the oxonium salt or sulfonium salt.

8. A method of preparing an onium salt comprising organic cations with $[PF_x(C_yF_{2y+1-z}H_z)_{6-x}]^-$, $[(BF_n(CN)_{4-n}]^-$, $[(R^{f1}SO_2)_2N]^-$ or $[BF_wR^{f2}_{4-w}]^-$ anions, comprising a reaction of an onium halide with an oxonium salt or sulfonium salt according to claim 1, where $R^o$, x, y, z, n, $R^f$, $R^{f2}$ and w have the meaning indicated for the oxonium salt or sulfonium salt.

9. A method according to claim 8, wherein the organic cation is a tritylium, ammonium, phosphonium, guanidinium, uronium, thiouronium cation or a heterocyclic cation.

10. A method according to claim 8, comprising reacting an onium halide with the oxonium salt or sulfonium salt.

11. A method for alkylating or catalyzing a cationic polymerisation or photochemically induced polymerisation, comprising providing as an alkylating agent or as a catalyst an oxonium salt or sulfonium salt according to claim 1 to a cationic polymerisation or photochemically induced polymerisation reaction.

12. An alkylating agent or catalysts for catalyzing a cationic polymerisation or photochemically induced polymerisation, comprising an oxonium salt or sulfonium salt according to claim 1.

13. An Oxonium salt according to claim 1 having $[(R^o)_3O]^+$ cations or sulfonium salt having $[(R^o)_3S]^+$ cations, where $R^o$ denotes straight-chain or branched alkyl group having 1-8 C atoms or unsubstituted phenyl or phenyl which is substituted by $R^o$, $OR^o$, $N(R^o)_2$, CN or halogen, and for the oxonium salt anions selected from the group consisting of $[PF_x(C_yF_{2y+1-z}H_z)_{6-x}]^-$ anions, where 2<x<5, 1<y<8 and 0<z<2y+1, or anions selected from the group consisting of $[(BF_n(CN)_{4-n}]^-$ anions, where n=0, 1, 2 or 3, or anions selected from the group consisting of $[(R^{f1}SO_2)_2N]^-$ anions, where $R^{f1}$ denotes F or perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups, or anions selected from the group consisting of $[BF_wR^{f2}_{4-w}]^-$ anions, where w=0, 1, 2 or 3, where $R^{f2}$ denotes perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups, where $R^{f1}$ or $R^{f2}$ may in each case be identical or different, and where, in $R^{f1}$ or $R^{f2}$, one or two non-adjacent carbon atoms of which are not in the α-position to the heteroatom may be replaced by atoms and/or atom groups selected from the group consisting of —O—, —SO$_2$— and —NR'— or by the end group —SO$_2$X', where R'=non-, partially- or perfluorinated $C_1$- to $C_6$-alkyl, $C_3$- to $C_7$-cycloalkyl, unsubstituted or substituted phenyl, or an unsubstituted or substituted heterocycle, and X'=F, Cl or Br, and for the sulfonium salt anions selected from the group consisting of $[(BF_n(CN)_{4-n}]^-$ anions, where n=0, 1, 2 or 3.

14. An sulfonium salt according to claim 1 having $[(R^o)_3S]^+$ cations and anions selected from the group consisting of $[(BF_n(CN)_{4-n}]^-$ anions, where n=0, 1, 2 or 3.

15. An sulfonium salt according to claim 1 having $[BF_3(CN)]^-$, $[BF_2(CN)_2]^-$, or $[B(CN)_4]^-$ anions and $[(C_2H_5)_3S]^+$ cations.

16. A salt (I) having cations selected from the group consisting of imidazolium, pyridinium, pyrimidinium, pyrazinium, quinolinium, isoquinolinium, and indolinium (with substituents $R^{1'}$, $R^{2'}$, $R^{3'}$, $R^{4'}$ as shown)

where
$R^{1'}$ denotes CN and
$R^{2'}$ to $R^{4'}$ each, independently of one another, have the meaning
hydrogen,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
dialkylamino containing alkyl groups having 1-4 C atoms, which, however, is not bonded to the heteroatom of the heterocycle,
saturated, partially unsaturated or fully unsaturated cycloalkyl having 3-7 C atoms,
which may be substituted by alkyl groups having 1-6 C atoms, or
aryl-$C_1$-$C_6$-alkyl,
where $R^{2'}$ and $R^{4'}$ may be partially or fully substituted by F,
where $R^{2'}$ and $R^{3'}$ may be partially or fully substituted by halogens or partially by $NO_2$ or CN, and
where, in $R^{2'}$ to $R^{4'}$, one or two non-adjacent carbon atoms which are not bonded directly to the heteroatom may be replaced by atoms and/or atom groups selected from the group consisting of —O—, —S—, —S(O)— and —$SO_2$—,
and
anions selected from the group consisting of $[PF_x(C_yF_{2y+1-z}H_z)_{6-x}]^-$ anions, where $2<x<5$, $1<y<8$ and $0<z<2y+1$,
or anions selected from the group consisting of $[(BF_n(CN)_{4-n}]^-$ anions, where n=0, 1, 2 or 3,
or anions selected from the group consisting of $[(R^{f1}SO_2)_2N]^-$ anions, where $R^{f1}$ denotes F or perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups,
or anions selected from the group consisting of $[BF_w R^{f2}_{4-w}]^-$ anions, where w=0, 1, 2 or 3, where $R^{f2}$ denotes perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups, where $R^{f1}$ or $R^{f2}$ may in each case be identical or different,
where a pair of $R^{f1}$ or a pair of $R^{f2}$ may be connected to one another by single or double bonds,
and where, in $R^{f1}$ or $R^{f2}$, one or two non-adjacent carbon atoms which are not in the α-position to the heteroatom may be replaced by atoms and/or atom groups selected from the group consisting of —O—, —$SO_2$— and —NR'— or by the end group —$SO_2$X', where R'=non-, partially- or per-fluorinated $C_1$- to $C_6$-alkyl, $C_3$- to $C_7$-cycloalkyl, unsubstituted or substituted phenyl, or an unsubstituted or substituted heterocycle, and X'=F, Cl or Br.

17. A salt according to claim 16, wherein the anions are $[(CF_3SO_2)_2N]^-$, $[(C_2F_5SO_2)_2N]^-$, $[(FSO_2)_2N]^-$, $[P(C_2F_5)_3F_3]^-$, $[P(CF_3)_3F_3]^-$, $[P(C_2F_4H)(CF_3)_2F_3]^-$, $[P(C_2F_3H_2)_3F_3]^-$, $[P(C_2F_5)(CF_3)_2F_3]^-$, $[P(C_3F_7)_3F_3]^-$, $[P(C_4F_9)_3F_3]^-$, $[P(C_2F_5)_2F_4]^-$, $[BF_3(CF_3)]^-$, $[BF_2(C_2F_5)_2]^-$, $[BF_3(C_2F_5)]^-$, $[BF_2(CF_3)_2]^-$, $[B(C_2F_5)_4]^-$, $[BF_3(CN)]^-$, $[BF_2(CN)_2]^-$, $[B(CN)_4]^-$, or $[B(CF_3)_4]^-$ anions.

18. A solvent, solvent additive, phase-transfer catalyst, extractant, heat-transfer medium, surface-active substance, plasticiser, flameproofing agent or conductive salt for electrochemical cells, comprising a salt according to claim 16.

19. A method for cyanation or activation, comprising providing as a cyanation or activation reagent a salt according to claim 16 to a cyanation reaction or reaction in need of activation.

20. A cyanation or activation reagent, comprising a salt according to claim 16.

21. A salt (I) according to claim 16 having cations selected from the group consisting of

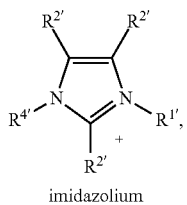
imidazolium

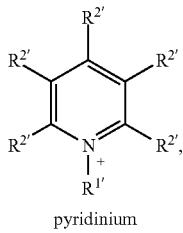
pyridinium

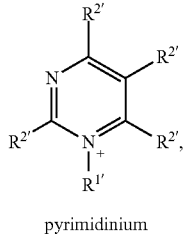
pyrimidinium

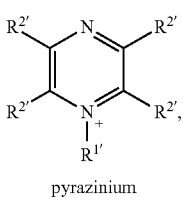
pyrazinium

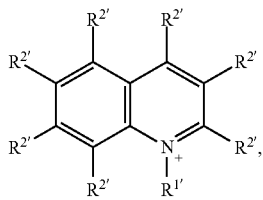
quinolinium

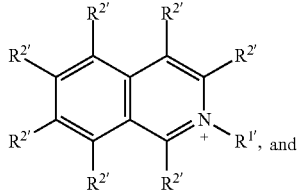
isoquinolinium

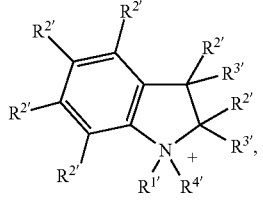
indolinium where
R$^{1'}$ denotes CN and
R$^{2'}$ to R$^{4'}$ each, independently of one another, have the meaning hydrogen,
 straight-chain or branched alkyl having 1-20 C atoms,
 straight-chain or branched alkenyl having 2-20 C atoms and one or more double bonds,
 straight-chain or branched alkynyl having 2-20 C atoms and one or more triple bonds,
 dialkylamino containing alkyl groups having 1-4 C atoms, which, however, is not bonded to the heteroatom of the heterocycle,
 saturated, partially unsaturated or fully unsaturated cycloalkyl having 3-7 C atoms,
 which may be substituted by alkyl groups having 1-6 C atoms, or
 aryl-C$_1$-C$_6$-alkyl,
where R$^{2'}$ and R$^{4'}$ may be partially or fully substituted by F,
where R$^{2'}$ and R$^{3'}$ may be partially or fully substituted by halogens or partially by NO$_2$ or CN, and
where, in R$^{2'}$ to R$^{4'}$, one or two non-adjacent carbon atoms which are not bonded directly to the heteroatom may be replaced by atoms and/or atom groups selected from the group consisting of —O—, —S—, —S(O)— and —SO$_2$—,
and
anions selected from the group consisting of [PF$_x$(C$_y$F$_{2y+1-z}$H$_z$)$_{6-x}$]$^-$ anions, where 2<x<5, 1<y<8 and 0<z<2y+1,
or anions selected from the group consisting of [(BF$_n$(CN)$_{4-n}$]$^-$ anions, where n=0, 1, 2 or 3,
or anions selected from the group consisting of [(R$^{f1}$SO$_2$)$_2$N]$^-$ anions, where R$^{f1}$ denotes F or perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups,
or anions selected from the group consisting of [BF$_w$R$^{f2}_{4-w}$]$^-$ anions, where w=0, 1, 2 or 3, where R$^{f2}$ denotes perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups,
where R$^{f1}$ or R$^{f2}$ may in each case be identical or different,
and where, in R$^{f1}$ or R$^{f2}$, one or two non-adjacent carbon atoms which are not in the α-position to the heteroatom may be replaced by atoms and/or atom groups selected from the group consisting of —O—, —SO$_2$— and —NR'— or by the end group —SO$_2$X', where R'=non-, partially- or per-fluorinated C$_1$- to C$_6$-alkyl, C$_3$- to C$_7$-cycloalkyl, unsubstituted or substituted phenyl, or an unsubstituted or substituted heterocycle, and X'=F, Cl or Br.

22. A salt according to claim 16, which contains
anions selected from the group consisting of [PF$_x$(C$_y$F$_{2y+1-z}$H$_z$)$_{6-x}$]$^-$ anions, where 2<x<5, 1<y<8 and 0<z<2y+1,
or anions selected from the group consisting of [(BF$_n$(CN)$_{4-n}$]$^-$ anions, where n=0, 1, 2 or 3,
or anions selected from the group consisting of [(R$^{f1}$SO$_2$)$_2$N]$^-$ anions, where R$^{f1}$ denotes F or perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups, or anions selected from the group consisting of [BF$_w$R$^{f2}_{4-w}$]$^-$ anions, where w=0, 1, 2 or 3, where R$^{f2}$ denotes perfluorinated straight-chain or branched alkyl having 1-20 C atoms, perfluorinated straight-chain or branched alkenyl having 2-20 C atoms and one or more double bonds, perfluorinated straight-chain or branched alkynyl having 2-20 C atoms and one or more triple bonds, perfluorinated, saturated, partially unsaturated or fully unsaturated cycloalkyl having 3-7 C atoms, which may be substituted by perfluoroalkyl groups, where $R^{f1}$ or $R^{f2}$ may in each case be identical or different, where a pair of $R^{f1}$ or a pair of $R^{f2}$ may be connected to one another by single or double bonds, and where, in $R^{f1}$ or $R^{f2}$, one or two non-adjacent carbon atoms which are not in the α-position to the heteroatom may be replaced by atoms and/or atom groups selected from the group consisting of —O—, —SO$_2$— and —NR'— or by the end group —SO$_2$X', where R'=non-, partially- or per-fluorinated $C_1$- to $C_6$-alkyl, $C_3$- to $C_7$-cycloalkyl, unsubstituted or substituted phenyl, or an unsubstituted or substituted heterocycle, and X'=F, Cl or Br.

23. A process for preparing an onium salt comprising organic cations with $[PF_x(C_yF_{2y+1-z}H_z)_{6-x}]^-$ anions, comprising reacting an onium tetrafluoroborate or hexafluorophosphate with a phosphorane of formula $PF_a(C_yF_{2y+1-z}H_z)_{5-a}$, where 1<a<4, 1<y<8 and 0<z<2y+1.

24. A process according to claim 23, wherein the organic cation is an ammonium, phosphonium, guanidinium, uronium, thiouronium cation or a heterocyclic cation.

* * * * *